United States Patent [19]

Chupp et al.

[11] 4,258,196

[45] Mar. 24, 1981

[54] PROCESS FOR THE PRODUCTION OF TERTIARY 2-HALOACETAMIDES

[75] Inventors: John P. Chupp; Richard D. Goodin, both of St. Louis, Mo.

[73] Assignee: Monsanto Company, St. Louis, Mo.

[21] Appl. No.: 63,005

[22] Filed: Aug. 2, 1979

Related U.S. Application Data

[63] Continuation-in-part of Ser. No. 896,879, Apr. 17, 1978, abandoned.

[51] Int. Cl.³ ................... C07C 102/00; C07D 277/62
[52] U.S. Cl. ............................ 548/165; 260/326 N; 260/347.3; 564/182; 260/465 D; 564/191; 564/209; 564/210; 564/212; 548/212; 560/155; 560/172
[58] Field of Search .............................. 548/212, 165; 260/561 HL, 562 B, 561 S, 562 S, 465 D, 448.2 N, 347.3, 326 N, 556 A; 560/155, 172

[56] References Cited

U.S. PATENT DOCUMENTS 3,992,432  11/1976  Napier et al. .................. 260/465.1

FOREIGN PATENT DOCUMENTS 1377225  12/1974  United Kingdom .

OTHER PUBLICATIONS

Kakimoto et al., Chemistry Letters, pp. 47–48 (1976).
Sorel et al., J. Org. Chem. 23 pp. 330–331 (1958).

*Primary Examiner*—Thomas A. Waltz
*Attorney, Agent, or Firm*—William I. Andress; Donald W. Peterson

[57] ABSTRACT

The disclosure herein relates to a novel process for producing tertiary 2-haloacetamides by reacting primary or secondary 2-haloacetamides with an agent capable of generating an anion of the primary or secondary 2-haloacetamide under base conditions and alkylating the anion of the 2-haloamide with an alkylating agent; said anion is generated, for example, by electrolysis or by metals, metal hydrides, fluorides, oxides, hydroxides, carbonates, phosphates, or alkoxides.

75 Claims, No Drawings

PROCESS FOR THE PRODUCTION OF TERTIARY 2-HALOACETAMIDES

CROSS-REFERENCE TO RELATED APPLICATION

This application is a continuation-in-part of U.S. Application Ser. No. 896,879 filed Apr. 17, 1978, now abandoned the whole of which is incorporated herein by reference.

BACKGROUND OF THE INVENTION

1. Field of the Invention

The invention herein relates to the field of chemical processes for the preparation of 2-haloacetamides, particularly those having as one nitrogen substituent an alkyl, alkenyl, alkynyl, alkoxyalkyl or heterocycyl group and, additionally, an alkenyl or cycloalkenyl radical or a phenyl group substituted with various radicals.

2. Description of the Prior Art 2-haloacetamides of the types described herein have been prepared by a variety of means known to the prior art. In one prior art process, described in U.S. Pat. No. 2,863,752 (Re 26,961) N-substituted-2-haloacetanilides are prepared by reacting a primary or secondary amine with the acid chloride of haloacetic acid typically in the presence of caustic soda to neutralize the by-product hydrogen halide. A similar process is described in German OLS No. 1,903,198 and U.S. Pat. Nos. 3,937,730 and 3,952,056 wherein the intermediates and final products are characterized by the N-substituent lower alkoxyethyl wherein the ethyl radical may have one or two methyl groups attached thereto.

In yet another prior art process described in U.S. Pat. No. 3,574,746, N-substituted-N-cycloalkenyl-2-haloacetamides are prepared by the haloacetylation of the corresponding N-substituted-cycloalkylidene amine in the presence of an acid acceptor.

In U.S. Pat. Nos. 3,630,716 and 3,637,847 a process is described for producing a-haloacetanilides which comprises reacting an aromatic amine with formaldehyde to produce the corresponding N-methylene amine (or azomethine) which is then reacted with a haloacetylating agent to produce the corresponding N-(halomethyl)-substituted 2-haloacetanilide. The latter product itself has herbicidal properties, but can further be reacted with an alcohol to produce the corresponding herbicidal N-(alkoxymethyl)-2-haloacetanilides as described in U.S. Pat. Nos. 3,442,945 and 3,547,620. In an analogous manner, the above process is described as useful for producing aliphatic 2-haloacetamides in U.S. Pat. No. 3,287,106.

Another process of the prior art for producing 2-haloacetamides involves the reaction of an appropriate aldehyde or ketone with an appropriate primary amine to produce the corresponding Schiff base which is then reacted with a haloacetic acid halide with the elimination of hydrogen chloride. See South African Pat. No. 753,918 and J. P. Chupp et al J.O.C. 33, 2357 (1968).

Still another process of the prior art for producing secondary 2-halo-N-(1-alken-1-yl) acetamides is to react chloracetamide with the appropriate aldehyde under conditions that eliminate water. See, e.g., German Pat. No. 2,155,494.

U.S. Pat. Nos. 4,025,648, 4,046,911 and 4,032,657 describe processes for producing fungicidal acetanilides or 2-haloacetanilides by acylating ('911 patent) or haloacylating the corresponding N-alkylated aniline.

The process of the present invention involves successfully alkylating primary or secondary 2halo amides under anion-forming conditions to produce useful tertiary 2-haloacetamides. That this process is totally novel and unexpected is made apparent by consideration of numerous criteria discussed below. In the discussion below the terms "alkylation" or "alkylating" are used generically to include reactions which give rise to various substituents (not just alkyl groups) on the primary or secondary amide anion.

Alkylation of amides via the anion is well known in the prior art, but care is taken to avoid substrates containing labile moieties which would interfere with the reaction. Furthermore, in alkylation of amidic-type materials, by-product imidate sometimes forms, arising from oxygen alkylation rather than nitrogen alkylation of the secondary amide (see for instance, J. R. Pougny et al, Organic Preparations and Procedures Int. 9, 5–8 (1977)). This side reaction has the effect of unpredictably reducing yields of the desired tertiary amide.

As illustrative of prior art amide alkylations, one process is described in the prior art wherein N-1-cyclohexen-1-yl) acetamide is reacted with sodium hydride at room temperature, with N-alkylation by methyl iodide, to give the N-methyl-N-cyclohexen-1-yl acetamide in good yield. R. B. Boar et al, J.C.S. Perkin I. 1237 (1975). In like manner, other investigators demonstrated that formamide and secondary formamide could be successfully N-alkylated with chloromethyl methyl ether via amide anion generation with sodium hydride (V. Schollkopf et al, "Angew. Chem." (English Ed.) 15 (1976); German Ed. 88, 296 (1976). G. L. Isele et al (Synthesis, pages 266–68 (1971) describe amide N-alkylation with hydrocarbyl halides in KOH/dimethylsulfoxide media. Similarly, Brehme disclosed the alkylation of acylanilines with methyl iodide under basic conditions in the presence of a phase transfer catalyst to produce the corresponding N-methylated acetanilide. See Synthesis, 113–114 (1976).

In the above-mentioned U.S. 4,032,657 patent, reference is made to an amide anion alkylation process wherein the acyl moiety of the secondary amide was deemed to be inert under conditions of the reaction.

It is not known in the prior art to alkylate anions of primary and secondary 2-haloacetamides to produce tertiary 2-haloacetamides, i.e., the process of the present invention. These 2-haloacetamide compounds have highly effective biological properties, e.g., as herbicides and plant growth regulators and safeners or as fungicides.

When prior workers have formed the anion of secondary or tertiary 2-haloacetamides, a variety of products have resulted, arising from elimination of the single alpha-halogen which is well known for its lability and facile displacement in 2-haloacetamides under a variety of conditions, including those of anion formation. For example, the low temperature treatment of certain secondary 2-haloacetamides with potassium, KOH or potassium t-butoxide as strong bases resulted in facile loss of halogen and the formation of diketopiperazines, α-lactams (aziridinones) or ring-opened products of the latter. See exemplary work by J. C. Sheenan et al as reported in articles in J.A.C.S. 83, 4792 (1961); ibid 86, 746 and 1356 (1964); ibid 89, 362, 366 (1967); ibid 91, 1176, 4596 (1969); ibid 95, 3415 (1973) and in J.O.C. 31 4244 (1966); ibid 35, 4246 (1970); by S. Sarel in J.A.C.S.

82, 4752 (1960) and in J.O.C. 23, 330 (1958) and by Baumgarten et al in J.A.C.S. 83, 4469 (1961); ibid 85, 3303 (1963) and by Baumgarten in J.A.C.S. 84, 4975 (1962); M. Kakimoto et al, Chemistry Letters, 47–48, 1976. N-alkylations via Michael-type additions to activated olefins are also known. See B. C. Challis et al, The Chemistry of Amides, pages 748–753 (1970); The Chemistry of Functional Groups, Ed. J. Zabicky, Interscience (Publisher).

Tertiary 2-haloacetamides are known to be not particularly stable to strong base under anion forming conditions; by themselves they can be easily transformed, with loss of α-halogen, to carbenoid intermediates and thence to olefins, and/or cyclopropane derivatives and the like or, in the presence of alkylating agents such as aldehydes and ketones, halogen is lost with formation of glycidic amides or degradation products therefrom. See, e.g., A. J. Speziale et al, J.O.C. 30, 1199 (1965); ibid 26, 3176 (1961) and B. G. Chatterjee et al, J.O.C. 30, 4101 (1965).

Therefore, the prior art relevant to amide alkylations exemplified above teaches that on treatment of 2-haloacetamides under anion-forming conditions, alpha-halogen is eliminated or indeed the alpha-methylene moiety destroyed, giving rise to entirely different products than those predicted on simple N-alkylation described below.

The prior art processes described above have certain inherent limitations and disadvantages. For example, the azomethine process referred to above in U.S. Pat. Nos. 3,630,716 and 3,637,847 is generally restricted to the use of basic or electron-rich primary anilines as starting materials. As electron withdrawing groups are increasingly substituted onto the aryl ring, condensation of the aniline with formaldehyde to form azomethine or the latter with haloacetyl halide becomes increasingly inhibited and finally largely inoperative. Thus the azomethine process gives poor or completely unsuccessful results in the production of herbicidally useful N-(alkoxymethyl) 2-haloacetanilide variously substituted, particularly in the ortho position, with alkoxy, halogen, nitro, trifluoromethyl and other electron-withdrawing groups.

Yet another limitation on the azomethine process is the inability to produce N-(1-alkoxy-1-ethyl) or N-(1-alkoxy-1-propyl)-2-haloacetanilides from the corresponding N-ethylidene or N-propylidene anilines. When these Schiff bases are reacted with an acetylating agent, e.g., chloroacetyl chloride, the resulting adducts are not stable and unlike similar adducts from the azomethines and chloroacetyl chloride, cannot be successfully reacted with alcohols to give desired N-(alkoxyalkyl) substitution. Rather, hydrogen chloride is eliminated to form N-alkenyl-2-haloacetanilides.

Yet another limitation identified in the prior art is the inability to produce N-(alkoxymethyl)-N-(1-cyclohexen-1-yl)-2-haloacetamides. Thus, 1-cyclohexen-1-yl amines are generally unknown and therefore unavailable for reaction with formaldehyde to form the requisite N-(1-cyclohexen-1-yl) azomethine. Moreover, the known tautomers, i.e., ring substituted N-(cyclohexylidene) amines are strongly resistant to azomethine formation. Furthermore, although N-substituted N-(cyclohexylidene) amines (i.e., imines), are known and provide the necessary starting materials for N-(substituted)-N-(1-cyclohexen-1-yl) 2-haloacetamides (U.S. Pat. No. 3,574,746), imine formation is conditioned on the availability of ketone and primary amine. This availability is completely lacking in the case of primary alkoxymethyl amines owing to their inherent instability and non-existence. Thus, N-(alkoxymethyl)-N-(1-cyclohexen-1-yl)-2-haloacetamides are also unavailable by the aforementioned ketimine route. The above considerations also apply to the acyclic N-(1-alken-1-yl)-2-haloacetamides, such that those materials likewise are incapable of materializing by known routes.

It is apparent from the above that in the aforementioned U.S. Pat. No. 3,574,746 and South African Patent No. 753,918, the disclosed processes can be used to produce only 2-haloacetamides having no less than two carbon atoms between the nitrogen and oxygen atoms of the N-(alkoxyalkyl) moiety.

One further limitation noted in prior art processes was the difficult, if not impossible, reaction of certain substituted phenyl-N-(halomethyl)-2-haloacetanilides with methyl mercaptan or salts. Thus, attempts to prepare thio-alachlor, i.e., 2',6'-diethyl-N-(methylthiomethyl)-2-chloroacetanilide, by the reaction of methyl mercaptan or its salt with the corresponding N-chloromethyl intermediates were unsuccessful.

It is therefore a primary object of this invention to provide a novel process for preparing in situ anions of secondary 2-haloacetamides as intermediate species which when reacted with other starting materials from hindered or unhindered tertiary 2-haloacetamides, which process suffers none of the above-mentioned disadvantages.

It is a further object of this invention to provide a simple and economic process for the production of 2-haloacetamides which can be substituted on the amide nitrogen with aliphatic, cycloaliphatic and/or aromatic substituents in high yield and assay.

Still another object of this invention is the provision of a process which can produce for the first time 2-haloacetamides which can be substituted on the amide nitrogen atom simultaneously with alkoxymethyl and cycloalkenyl (e.g., 1-cycloalken-1-yl) radicals.

These are other objects will become apparent from the detailed description below.

SUMMARY OF THE INVENTION

The present invention relates to a process for the preparation of 2-haloacetamides having the formula

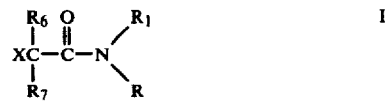

which comprises converting a secondary 2-haloacetamide of the formula

to an anion thereof in either stoichiometric or incremental amounts under basic conditions by means of electrolysis or reaction with elemental metals, metal fluorides, hydrides, oxides, hydroxides, carbonates or alkoxides, the preferred metals being alkali and alkaline earth metals, and reacting said anion preferably in situ with a compound of the formula $R_1X^1$     III or a Michael (1,4—) addition reagent such as α,β-unsaturated acid or carbonyl derivatives having up to 8 carbon atoms exemplified by acrylonitrile, ethyl acrylate, diethylmaleate, acetylenedicarboxylate, acrolein, etc., wherein in the above formula:

X is chlorine, bromine or iodine;

$X^1$ is chlorine, bromine, iodine or a halogen equivalent such as p-toluenesulfonate, methyl sulfate ($CH_3OSO_3$—); or other moiety recognized for its lability (but otherwise inertness);

R is hydrogen, $C_{1-18}$ alkyl, $C_{2-18}$ alkenyl, alkynyl or alkoxyalkyl, polyalkoxyalkyl, $C_{3-7}$ cycloalkyl or cycloalkylalkyl, $C_{5-7}$ cycloalkenyl or cycloalkadienyl which may be substituted with $C_{1-6}$ alkyl groups; saturated or unsaturated heterocyclic radicals having up to 6 ring atoms containing O, $S(O)_a$ and/or $N(R_5)_b$ groups or a radical of the formula

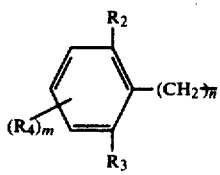

IV wherein a is 0–2 inclusive;

b and n are 0 or 1;

m is 0–3 inclusive when $R_2$ and $R_3$ are other than hydrogen and 0–5 otherwise;

$R_2$, $R_3$, $R_4$ and $R_5$ are independently hydrogen, $C_{1-6}$ alkyl, alkoxy, polyalkoxy, or alkoxyalkyl, $C_{2-6}$ alkenyl, alkenyloxy, alkynyl or alkynyloxy, $C_{6-10}$ aryl, aryloxy, aralkyl or aralkyloxy, $NO_2$, halogen, $CF_3$—, $(CH_3)_3Si$—, saturated or unsaturated heterocyclic radical having up to 6 ring atoms contianing O, $S(O)_a$ and/or $N(R_5)_b$ groups or $R_2$, $R_3$, $R_4$ when combined with the phenyl radical to which attached may form a $C_{6-10}$ aryl radical; or, when not a hydrogen atom, the R group may be substituted with an $R_2$-$R_5$ group;

$R_1$ is $C_{1-18}$ alkyl, $C_{3-18}$ alkenyl or alkynyl, $C_{2-18}$ alkoxyalkyl, $C_{3-7}$ cycloalkyl or cycloalkylalkyl, $C_{6-10}$ aralkyl, alkylthiomethyl cyanomethyl, loweracyloxymethyl, hydrocarbyloxycarbomethyl wherein the hydrocarbyl moiety is a $C_{1-4}$ alkyl or aralkyl radical having up to 10 carbon atoms, e.g., benzyl, and the methyl radical in said carbomethyl moiety may be substituted with $C_{1-4}$ alkyl, phenyl, benzyl, etc; loweralkylthiocarbomethyl, substituted or unsubstituted carbamoylmethyl, benzothiazolinonylmethyl, phthalimidomethyl, mono- or di-loweracylamidomethyl or $C_{1-10}$ hydrocarbylsulfonylamidomethyl groups or said $R_1$ member substituted with an $R_2$-$R_5$ member which is inert under reaction conditions, provided that when $R_1$ is an alkenyl radical it cannot have an olefinic bond on the carbon atom attached to the nitrogen atom and $R_6$ and $R_7$ are independently hydrogen or alkyl, cycloalkyl, cycloalkenyl, alkenyl or aromatic hydrocarbon each having up to 12 carbon atoms.

A subgenus of compounds of particular interest which may be prepared by the process of this invention are 2-haloacetamides which are substituted on the amide nitrogen simultaneously with 1-cycloalken-1-yl and alkoxymethyl radicals which may further be substituted with groups which are nonreactive in the process.

Another subgenus of compounds of special interest which are prepared by the process of this invention are 2-haloacetanilides substituted on the amide nitrogen with hydrogen, $C_{1-10}$ alkyl or alkoxyakyl radicals, such as alkoxymethyl and alkoxyethyl wherein the anilide ring may be unsubstituted or which may be substituted with non-interfering groups such as $C_{1-8}$ alkyl, alkoxy, akoxyalkyl, nitro, halogen, e.g., chlorine, bromine, iodine or fluorine, trifluoromethyl and the like.

Yet another preferred subgenus of compounds prepared by the process of this invention are 2-haloacetamides which are substituted on the amide nitrogen atom simultaneously with alkoxyalkyl radicals, e.g., alkoxymethyl, alkoxyethyl or alkoxyprop-2-yl radicals and alken-1-yl radicals which also may be substituted with non-interfering radicals.

Preferred secondary 2-haloacetamide starting materials are those required to produce the above-mentioned tertiary 2-haloacetamides of particular interest in the process of this invention.

Preferred "alkylating agents", e.g., compounds of Formula III above, are those compounds which donate the nonhaloacyl substituent on the subgenera of compounds mentioned above. Compounds suitable for alkylating agents include the haloalkyl alkyl ethers, e.g., chloromethyl methyl ether, 2-bromoethyl methyl ether, halomethylthioethers, etc., but certain other ethers, e.g., 2-chloroethyl ethyl ether may be too sluggish for practical use. Other suitable alkylating agents include $C_{1-4}$ alkyl sulfates, e.g., dimethylsulfate, diethylsulfate, and $C_{1-10}$ alkyl toluene sulfonate esters, e.g., methyl p-toluenesulfonate, etc. Other alkylators include the halides of aliphatic and arylalkyl aromatic compounds, e.g., alkyl, alkenyl, alkynyl, and benzyl halides, such as methyl iodide, benzyl bromide, ethyl bromide, allyl chloride, bromide or iodide and propargyl bromide or iodide (the chloride is too sluggish). Also suitable alkylating agents are N-(halomethyl)-substituted acylamides and acetanilides or the 2-haloanalogs thereof, e.g., N-(chloromethyl) acetamides, 2',6'-dialkyl-N-(chloromethyl)-2-chloro-acylanilide and heterocyclics, e.g., halomethyl-substituted benzo-, thieno- or pyridoheterocycles, e.g., 3-(chloromethyl)-2-benzothiazolinone. Other reactive alkylating agents within the purview of this invention include O-(halomethyl) esters of aliphatic or aromatic acids such as chloromethyl acetate or bromomethyl benzoate and aliphatic and aromatic esters of α-haloalkanoic acid such as ethyl bromoacetate, benzyl chloroacetate, methyl-2-bromopropionate, etc. Specific examples of other alkylating agents include N-(bromomethyl) phthalimide, chloromethyl pivaloate, chloroacetonitrile.

The process of this invention is preferably conducted in the presence of a phase transfer catalyst such as polyethers or quaternary ammonium halide salts as described in more detail below.

DETAILED DESCRIPTION OF THE INVENTION

The process of the present invention may be practiced in any of the embodiments described herein.

(A) A preferred embodiment of the present process utilizes a multiphase system employing a base sufficiently strong enough to react with the starting secamide, optionally dissolved in an organic solvent, mainly at the interface, to produce incremental concentrations of amide anion. The presence of a phase transfer catalyst permits the so-formed amide anion to be transported via ion pair into the organic portion wherein most of the alkylating agent (i.e., compound of Formula III above) or activated olefin resides, and so react. The reaction will proceed without said catalyst, although yields are usually decreased, reaction times increased, and imidate by-product increased.

It will be understood that the weaker the acidity of the amide of Formula II, the stronger must be the base. Thus, e.g., weakly acidic amides such as the starting materials for preparing alachlor (Example 13) or N-(2,6-dimethyl-1-cyclohexen-1-yl)-N-(methoxymethyl)-2-chloroacetamide (Example 1), namely, 2',6'-diethyl-2-chloracetanilide and N-(2,6-dimethyl-1-cyclohexen-1-yl)-2-chloracetamide require in this embodiment, strong bases such as aqueous or solid sodium hydroxide or potassium hydroxide. Further, it is preferred when aqueous caustic is used that the solution be concentrated; (i.e., 20–50%).

On the other hand, in the alkylation of strongly acidic materials such as 2-chloro-2',6'-dinitroacetanilide, it can be demonstrated that a weaker base such as solid or aqueous sodium carbonate can be used to successfully generate amide anion and consequently effect alkylation (Example 17).

It will be appreciated that the amide anion in this embodiment A will form an ion pair with the cation of the phase transfer catalyst. Therefore, useful catalysts are those containing organic-soluble cations such as those enumerated in U.S. Pat. No. 3,992,432, including ammonium, phosphonium and sulfonium salts. Exemplary phase transfer catalysts include quaternary ammonium salts, e.g., aryl or aralkyl trialkyl ammonium halide salts such as benzyl triethyl ammonium bromide or chloride. Other phase transfer catalysts include the acyclic and cyclic poly ethers which complex with the base cation and then pair with amide anion as counter ion for transport to the organic phase for alkylation. Exemplary of such catalysts would include "18-crown-6" cyclic ether in combination with potassium hydroxide or fluoride as base.

Other bases in this embodiment A, dependent, however, on sec-amide acidity are alkali metal hydroxides, carbonates, and phosphates and alkaline earth hydroxides, e.g., calcium oxide or hydroxide, trisodium phosphate, potassium carbonate.

Inert solvents for use in this embodiment A include, e.g., esters of alkanoic acids and alkanols such as ethyl acetate, etc., dichloromethane, benzene, chlorobenzene, tetrahydrofuran, dimethyl sulfoxide, dimethylformamide, toluene, diethyl ether, except that when aqueous bases are used, the solvent should be appreciably water insoluble.

(B) A second embodiment of the present invention utilizes two different modifications to overcome by-product imidate formation (formed via O-alkylation). In the first, when small amounts of starting amide are used, i.e., up to about 50 g, phase transfer catalyst is increased to about 20–50% by weight of the amide charged, mixed with alkylating agent and the base added last. A second method, particularly useful for preparing large amounts of tertiary amide is to wash the reaction mixture (minus the base or aqueous phase) with dilute acid, preferably 5%–10% HCl solution, wherein the imidate, but not the tertiary amide product, is converted to starting sec-amide. This mixture of amides can then be treated with fresh alkylating agent, catalyst and base to effect conversion of remaining sec-amide to tert amide. It will be appreciated that such transformation of imidate to desired amide product can be effected in a recycling process either through a stepwise procedure, or by use of suitably designed equipment, as in a continuous or cascade process.

(C) Another embodiment of the present process employs a reactive metal, metal hydride or organometallic base to effect stoichiometric conversion of starting amide to amide anion. Exemplary is the addition of a dry ether or tetrahydrofuran solution of a secondary 2-chloroacetamide to an excess of potassium hydride, slurried in the same solvent. Liberation of hydrogen occurs immediately, and in theory amount. The amide anion salt can then be reacted by addition of excess alkylating agent. Excess hydride is destroyed with water, and the tert-amide isolated as described in examples below. This embodiment has the advantages of minimizing imidate and diketopiperazine formation while preserving the alkylating agent which otherwise may be sensitive to aqueous base.

In considering embodiments of A, B and C, the ratios of reactants in these processes are not critical, but are dictated primarily be economic considerations and avoidance of unwanted by-products. Hence, large excesses or deficiencies ot any expensive component relative to another component should be avoided. Embodiment A is best conducted with an excess of NaOH.

The process of this invention may be carried out at temperatures ranging from subzero to ambient or higher, e.g., from $-20°$ to $+100°$ C., but usually room temperatures are sufficient, and desirable.

(D) Another embodiment of this invention involves the generation of the secondary amide anion by electrolytic means. In electrolytic processes, the amide anion is generated directly at a suitable cathode. The resulting anion is alkylated with an appropriate compound of Formula III above, e.g., haloalkyl alkyl ethers such as chloromethyl methyl ether.

The above embodiments are exemplified in the specific working examples which follow.

EXAMPLE 1

This example exemplifies preferred embodiments (A) and (B) of the present process utilizing a multiphase system to generate a stable 2-haloacetamide anion and "alkylation" of same with a compound according to Formula III above in the presence of a phase-transfer catalyst to produce the corresponding stable tertiary 2-haloacetamide. Part (a) describes the preparation of the secondary 2-haloacetamide starting material and Part (b) describes the generation of the amide anion and alkylation thereof.

(a) A reaction vessel is charged with 11.3 parts of chloroacetyl chloride, 150 parts of chlorobenzene and 25 parts of N-2,6-dimethylcyclohexylidene amine. The reaction mixture is refluxed for several hours, cooled and filtered to obtain 13.5 parts of solid product, M.P. 114°–115° C.

Calc'd for $C_{10}H_{17}ONCl$ (percent); Cl, 17.55; N, 6.93
Found: Cl, 17.86; N, 7.02

The product was identified as N-(2,6-dimethyl-1-cyclohexen-1-yl)-2-chloroacetamide.

(b) A mixture of 400 g. of the sec-amide produced above in 760 ml methylene chloride and 300 ml chloromethyl methyl ether were mixed with 2 g. benzyl triethyl ammonium bromide. The mixture was cooled to 10° C. then added in a thin stream over 0.5 hour to a vigorously stirred mixture of 1100 ml of 50% sodium hydroxide, 300 ml methylene chloride and 9 g. benzyl triethyl ammonium bromide contained in a 5-liter 4-necked round bottomed flask. Exterior cooling with an ice/acetone bath was necessary to maintain the temperature under 25° C. The mixture was stirred for an additional one hour. GLC showed 78% tertiary amide produced and 22% of corresponding O-alkylated by-product, O-(methoxymethyl)-N-(2,6-dimethyl-1-cyclohexen-1-yl)-2-chloroacetimidate. The reaction mixture was separated, and the organic layer given a simple wash with 5% HCl solution to convert the imidate to starting secondary amide. To the washed mixture in methylene chloride was added an additional 120 ml of chloromethyl methyl ether and 5.0 g of the quaternary ammonium phasetransfer catalyst, followed by 350 ml of 50% NaOH with stirring. After separation of layers and additional water washing, the product was filtered through clay; methylene chloride solvent was evaporated and the residue heated to 85° C. (0.55 mm), then filtered through clay to purify the product. The product was recovered in about 99% yield and had a boiling point of 127° (0.15 mm).

Calc'd for $C_{12}H_{20}ClNO_2$ (percent): C, 58.65; H, 8.20; N, 5.70; Found: C, 58.48; H, 8.22; N, 5.62.

The product was identified as N-(2,6-dimethyl-1-cyclohexen-1-yl)-N-(methoxymethyl)-2-chloroacetamide.

The above process in Part (b) may be performed without imidate formation thus obviating acid-catalyzed reformation of sec-amide when lesser quantities, i.e., up to 50 g. of the sec-amide are used, the catalyst concentration is increased up to 20-50% of the amount of sec-amide used and the base, NaOH, is added all at once.

Structure proof of the products obtained in this and the following examples was afforded by mass spectroscopy, gas liquid chromatography, nuclear magnetic resonance and elemental analysis.

EXAMPLE 2

In this example, a different alkylating agent is used to alkylate the anion of a sec-amide.

Ten (10) grams (0.05 mol) of N-(2,6-dimethyl-1-cyclohexen-1-yl)-2-chloroacetamide, 16 g of chloroacetonitrile, 2 g of benzyl triethyl ammonium bromide and 200 ml of methylene dichloride ($CH_2Cl_2$) were charged to a 500 ml 4-neck flask and cooled to 10° C. To this mixture was added all at once about 100 ml of 50% aqueous NaOH and allowed to exotherm to 30° C., then stirred overnight. Water was added and the mixture filtered through clay. The $CH_2Cl_2$ layer was separated, dried over $MgSO_4$ and filtered. GLC analysis showed 29% starting amide and 71% alkylated tertiary amide product. Evaporation left a black oily material which was passed through 115 g Florsil with chloroform; evaporation of the latter left 9.9 g of light yellow oil which was filtered through silica gel (150 g) with a 3:2 hexane/ether mixture. Evaporation of the solvent left 6 g light yellow oil which was distilled to give 5.1 g of light yellow oil, b.p. 150° C. at 0.05 mm; this oil solidified in the bottle. Yield 42%.

Calc'd for $C_{12}H_{17}ClN_2O_1$ (percent): C, 59.84; H, 7.14; N, 11.65 Found: C, 59.87; H, 7.12; N, 11.64

The product was identified as N-(2,6-dimethyl-1-cyclohexen-1-yl)-N-(cyanomethyl)-2-chloroacetamide.

EXAMPLE 3

In this example, the sec-amide anion was alkylated with O-(chloromethyl) pivalate.

Ten (10) grams (0.25 mol) of N-(2,6-dimethyl-1-cyclohexen-1-yl)-2-chloroacetamide, 15 g pivaloyloxymethylchloride, 2.0 ml of $CH_2Cl_2$ were charged to a 500 ml flask. About 100 ml of 50% NaOH was added all at once with good stirring, with exotherm to 32° C. After stirring 5 hours the contents clouded and salt precipitated. Water was added to dissolve the salt and the layers separated. The organic $CH_2Cl_2$ layer was dried over $MgSO_4$, filtered and solvent removed, in vacuo, leaving an amber oil. After filtering through silica gel with 3:2 hexane/ether and evaporation of solvent, an oil was obtained which upon distillation gave 2.1 g of product having b.p. 140° at 0.05 mm. Yield 13%.

Calc'd for $C_{16}H_{26}ClNO_3$ (Percent): C, 60.85; H, 8.30; N, 4.43 Found: C, 60.73; H, 8.33; N, 4.42

The product was identified as N-(2,6-dimethyl-1-cyclohexen-1-yl)-N-(pivaloyloxymethyl)-2-chloroacetamide.

EXAMPLE 4

Following generally the same procedure described in the preceding example, but substituting 3-(chloromethyl)-2-benzothiazolinone as the alkylating agent, 2.9 g of product m.p. 142°-144° C. Yield 40%.

Calc'd for $C_{18}H_{21}ClN_2O_2S$ (Percent): C, 59.25; H, 5.80; N, 7.69 Found: C, 59.11; H, 5.82; N, 7.69

The product was identified as N-(2,6-dimethyl-1-cyclohexen-1-yl)-N-[3-(2-benzothiazolinone) methyl]-2-chloroacetamide.

EXAMPLE 5

The above procedure was followed in general, but using N-(bromomethyl)phthalimide as the alkylating agent. A white solid, m.p. 167°-169° C., was recovered in an amount of 2.0 g. Yield 22%.

Calc'd for $C_{19}H_{21}ClN_2O_3$ (percent): C, 63.24; H, 5.87; N, 7.76 Found: C, 62.70; H, 5.83; N, 7.71

The product was identified as N-(phthalimidomethyl)-N-(2,6-dimethyl-1-cyclohexen-1-yl)-2-chloroacetamide.

EXAMPLE 6

The general procedure above was followed, but using acrylonitrile as the alkylating agent. Four and one-half (4.5) grams of light yellow oil product was obtained, b.p. 169°-173° C. at 0.05 mm. Yield 35%.

Calc'd for $C_{13}H_{19}ClN_2O$ (percent): C, 61.29: H, 7.52; N, 11.00 Found: C, 61.67; H, 7.60; N, 11.26

The product was identified as N-(2-cyanoethyl)-N-(2,6-dimethyl-1-cyclohexen-1-yl)-2-chloroacetamide.

EXAMPLE 7

In this example, the 2-halo sec-amide anion is alkylated with ethyl bromoacetate to produce the corresponding tertiary 2-halo acetamide.

N-(2,6-dimethylcyclohexen-1-yl)-2-chloroacetamide, 4.03 gms (0.02 mol) and 3.34 gms (0.02 mol) of ethyl bromoacetate, together with 2.0 gms of triethyl benzyl ammonium chloride, were dissolved in 100 ml $CH_2Cl_2$ and the temperature lowered in an ice/acetone bath. Fifty (50) ml of 50% NaOH were then added all at once. After about 5 minutes the reaction was indicated by GLC to be 90% completed. Ice water was added and the layers separated. The organic layer was washed with 2.5% NaCl, dried, filtered and stripped; at this stage the reaction was 95% completed. The mixture was allowed to stand at room temperature for about two days, but did not crystalize. The mixture was distilled to give a main fraction, b.p. 150° C. at 0.1 mm Hg. The product, 3.6 gms of a clear yellow oil, was obtained in 63% yield.

Calc'd for $C_{14}H_{22}ClNO_3$ (%): C, 58.43; H, 7.71; N, 4.87 Found: C, 58.19; H, 7.71; N, 4.86 The product was identified as N-(1-ethoxycarbonylmethyl)-N-(2,6-dimethyl-1-cyclohexen-1-yl)-2-chloroacetamide.

Examples 1-7 have exemplified embodiments of the process of this invention to prepare tertiary 2-haloacetamides substituted on the amide nitrogen atom with an N-(1-cyclohexen-1-yl) and another radical. In Examples 8 et seq., embodiments of this process will be described for the preparation of 2-haloacetanilide compounds substituted with various radicals on the amide nitrogen atom.

EXAMPLE 8

This example describes the preparation of an N,2'6'-trimethyl substituted acetanilide from the corresponding secamide anion formed by use of a solid base dissolved in a solvent, which anion is then alkylated with an ester of p-toluenesulfonic acid.

Two (2) gsm (0.01 mol) of N-(2,6-dimethyl)-2-chloroacetanilide, 3.7 gms (0.02) of methyl p-toluenesulfonate and 2.26 gms (0.02) of potassium carbonate ($K_2CO_3$) were mixed in about 25 ml of dimethylformamide and stirred at room temperature until the reaction was complete as indicated by glc. After 16.5 hours, the product was recovered as a colorless solid, m.p. 61°-62° C., in 58% yield.

Calc'd for $C_{11}H_{14}ClNO$ (%): C, 62.4; H, 6.7; Cl, 16.8 Found: C, 62.6; H, 6.8; Cl, 16.6

The product was identified as N-methyl-N-(2',6'-dimethyl)-2-chloroacetanilide.

EXAMPLE 9

This example describes the use of dimethyl sulfate as the alkylating agent to prepare an N-alkyl-2-chloroacetanilide from the corresponding sec-amide anion.

2'-n-butoxy-6'-methyl-2-chloroacetanilide, 4.9 gms (0.02 mol), dimethyl sulfate, 2.6 gms (0.02 mol) and 2.0 gms of triethyl benzyl ammonium bromide were mixed in 250 ml of $CH_2Cl_2$ under cooling. Fifty (50) of 50% NaOH were then added all at once at 15° C. and the mixture stirred for two hours. Water (100 ml) was added and the resultant layers separated. The organic layer was washed with water, dried over $MgSO_4$ and evaporated by Kugelrohr. A clear liquid, b.p. 135° C. at 0.07 mm Hg was obtained in 78% yield (4.2 gms) and recrystallized upon standing to a colorless yield, m.p. 41°-42.5° C.

Calc'd for $C_{14}H_{20}ClNO_2$ (%): C, 62.33; H, 7.47; Cl, 13.14 Found: C, 62.34; H, 7.49; Cl, 13.16

The product was identified as 2'-n-butoxy-6'-methyl-N-methyl-2-chloroacetanilide.

EXAMPLE 10

This example describes the preparation of an N-alkyl-2-haloacetanilide using an alkenyl halide as the alkylating agent.

2'-methoxy-6'-methyl-2-chloracetanilide, 4.7 gms (0.022 mol), 5.25 gms (0.044 mol) of 3-bromopropene and 2.0 gms of triethyl benzyl ammonium bromide were mixed in 250 ml of $CH_2Cl_2$ under cooling to 0° C. Fifty (50) ml of 50% NaOH were added all at once maintaining the temperature below 15° C. and stirred for 4.5 hours. Cold water (100 ml) was added and the layers separated. The organic layer was washed with water, dried over $MgSO_4$ and evaporated to leave a beige-colored solid product, m.p. 94.5°-96° C.

Calc'd for $C_{13}H_{16}ClNO_2$ (%): C, 61.54; H, 6.36; Cl, 13.97 Found: C, 61.66; H, 6.38; Cl, 13.24

The product was identified as 2'-methoxy-6'-methyl-N-allyl-2-chloroacetanilide.

EXAMPLE 11

Following the same general procedure described in Example 10, but substituting 2,3-dichloropropene, 5.6 gms (0.05 mol), as the alkylating agent for the anion of 2'-methoxy-6'-methyl-2-chloracetanilide, 5.3 gms (0.025 mol), 2.0 gm (27.8% yield) of an amber oil, b.p. 136° C. at 0.03 mm Hg (Kugelrohr), was obtained.

Calc'd for $C_{13}H_{15}Cl_2NO_2$ (%): C, 54.18; H, 5.25; Cl, 24.61 Found: C, 54.36; H, 5.30; Cl, 24.45

The product was identified as 2'-methoxy-6'-methyl-N-(2-chlorallyl)-2-chloroacetanilide.

EXAMPLE 12

2'-methyl-6'-methoxy-2-chloroacetanilide (4.3 g, 0.02 mol), propargyl bromide (4.8 g., 0.04 mol), 2.0 g benzyl triethyl ammonium bromide and 50 ml $CH_2Cl_2$ were mixed in a 500 ml 4-neck flask. 20 ml of 50% aqueous NaOH is added with stirring and cooling at 20° C. The mixture was stirred for 7 hours, water added and the formed organic layer separated and washed with a saturated NaCl solution, then dried over $MgSO_4$ and the $CH_2Cl_2$ evaporated. The residual solid was crystallized from methanol and filtered to give 4.9 g of crystalline prisms m.p. 124°-126° C. Yield 97.3%.

Calc'd for $C_{13}H_{14}ClNO_2$ (%): C, 62.03; H, 5.61; N, 5.56; Cl, 14.08 Found: C, 61.99; H, 5.65; N, 5.54; Cl, 14.10

The product was identified as 2'-methyl-6'-methoxy-N-(propargyl)-2-chloroacetanilide.

EXAMPLE 13

2-chloro-2',6'-diethylacetanilide (11.2 g, 0.05 mol) is dissolved in 200 ml methylene chloride with 3 g triethyl benzyl ammonium bromide and 10 ml chloromethyl methyl ether. To the rapidly-stirred solution at room temperature is added all at once, 70 ml 50% aqueous sodium hydroxide, with exterior cooling to prevent reaction temperatures exceeding 32° C. After addition, the mixture is stirred for ninety minutes, then a mixture of ice and water (ca 300 ml) added. The layers are separated, and the organic phase washed once again with 300 ml water. The methylene chloride is removed under vacuum to leave 13.1 g (97.4% yield) of oily residue as product, assaying by glc at 92.4%. Eight grams of this material was distilled under vacuum (b.p. 120°-130° C. at 0.5 mm) to give 7.9 g near colorless oil, assay 92.5% 2-chloro-N-(methoxymethyl)-2',6'-diethylacetanilide (alachlor).

Calc'd for $C_{14}H_{20}ClNO_2$ (%): C, 62.33; H, 7.47; Cl, 13.31; N, 5.19 Found: C, 62.20 H, 7.50; Cl, 13.31; N, 5.19

EXAMPLE 14

The process of Example 13 was repeated, but using 2'-tert-butyl-2-chloroacetanilide as the sec-amide. The residual oil remaining after evaporation of the solvent solidified on standing to give 5.8 g of product m.p. 68°-70° C.

The product was identified as 2'-tert-butyl-N-(methoxymethyl)-2-chloroacetanilide.

EXAMPLE 15

Following the above procedure, but using 2'-(methoxymethyl)-2-chloroacetanilide as the sec-amide starting material and chloromethyl methyl ether as the alkylating agent, the product 2'-(methoxymethyl)-N-(methoxymethyl)-2-chloroacetanilide was obtained.

EXAMPLE 16

2',6'-Dimethyl-2-chloroacetanilide (1.0 g, 5.1 mmol); dimethylsulfate (1.33 g, 10.6 mmol), potassium fluoride (0.58 g, 10.0 mmol) and "18-crown-6" cyclic ether (0.26 g, 1.0 mmol) were magnetically stirred in 20 ml acetonitrile at room temperature for 15 hours.

Acetonitrile was removed under reduced pressure. The residue was treated with ethyl ether and water. Ether layer was washed again with water and saturated sodium chloride, dried over magnesium sulfate and ether removed under reduced pressure leaving white solid.

Nmr and glc analysis indicates 15% conversion to 2',6'-dimethyl-N-(methyl)-2-chloroacetanilide.

EXAMPLE 17

2',6'-Dinitro-2-chloroacetanilide (2.4 g, 0.009 mol), 150 ml $CH_2Cl_2$, 1.1 g benzyl triethyl ammonium bromide and 3 ml chloromethyl propyl ether were first mixed, then 100 ml of saturated $Na_2CO_3$ added. On work-up, a dark oil was obtained and eluted through Florsil with $CH_2Cl_2$ to give 3.1 g of a yellow oil.

Calc'd for $C_{12}H_{14}ClN_3O_6$ (%): C, 43.45; H, 4.25; N, 12.67 Found: C, 43.41; H, 4.29; N, 12.20

The product was identified as 2'-6'-dinitro-N-(n-propoxymethyl)-2-chloroacetanilide.

EXAMPLE 18

In this example, 2'-methyl-6'-nitro-2-chloroacetanilide was used as the sec-amide and chloromethyl ethyl ether as the alkylating agent and 50% NaOH as the base. The product was 3.5 g of a white solid m.p. 96°–98° C., identified as 2'-methyl-6'-nitro-N-(ethoxymethyl)-2-chloroacetanilide.

EXAMPLE 19

The procedure described in Example 1 was repeated, but using 2'6'-dimethoxy-2-chloroacetanilide as the sec-amide. After work-up as before and evaporation of the solvent, 12.9 g of white solid was obtained which was recrystallized in isopropanol to give 11.8 g of white crystals, m.p. 104°–106° C., in 90% yield.

Calc'd for $C_{12}H_{16}ClNO_4$ (%): C, 52.66; H, 5.89; N, 5.12 Found: C, 52.58; H, 5.99; N, 5.10

The product was identified as 2',6'-dimethoxy-N-(methoxymethyl)-2-chloroacetanilide.

EXAMPLE 20

2,2',6'-trichloroacetanilide (7 g, 0.029 mol), chloromethyl ethyl ether (5.5 g, 0.058 mol), benzyl triethyl ammonium bromide (1.5 g) and 100 ml $CH_2Cl_2$ were charged to a 250 flask. 32 ml of 50% NaOH was added all at once, with exotherm to 36° C. and stirred for 0.5 hour. Water was added and after washing the $CH_2Cl_2$ layer separated, dried over $MgSO_4$, filtered and the solvent evaporated in vacuo leaving a white solid which was recrystallized from hexane to give 5.6 g of white solid, m.p. 80°–83° C. Yield 65%.

Calc'd for $C_{11}H_{12}Cl_3NO_2$ (%): C, 44.56; H, 4.08; N, 4.72; Found: C, 44.56; H, 4.11; N, 4.73

The product was identified as 2',6'-dichloro-N-(ethoxymethyl)-2-chloroacetanilide.

EXAMPLE 21

Following the above general procedure, 2',3',4',5',6'-pentafluoroacetanilide was alkylated with chloromethyl methyl ether to obtain 3.4 of a slight yellow oil, b.p. 123°–125° C. at 0.05 mm; yield 56%.

Calc'd for $C_{11}H_9ClF_5NO_2$ (%): C, 41.59; H, 2.86; N, 4.41 Found: C, 41.81; H, 2.71; N, 4.41

The product was identified as 2',3',4',5',6'-pentafluoro-N-(ethoxymethyl)-2-chloroacetanilide.

EXAMPLE 22

This example illustrates the preparation of a tertiary N-heterocyclic-2-haloacetamide from the sec-amide anion thereof.

Two (2) g of N-furfuryl-2-chloroacetamide were dissolved in benzene with 2 ml chloromethyl methyl ether in 150 ml of $CH_2Cl_2$ and 0.4 g benzyl triethyl ammonium bromide. Then 3 g of powdered NaOH were added. The mixture was stirred for ca 2 hours, allowed to settle, and the organic solution decanted, then washed with water. On evaporation, the residue was distilled and 1.3 g of product recovered, b.p. 130°–150° C. at 0.3 mm; yield 52%.

Calc'd for $C_9H_{12}ClNO_3$ (%): C, 49.67; H, 5.56; N, 6.44 Found: C, 49.10; H, 5.45; N, 6.18

The product was identified as N-(methoxymethyl)-N-(furfuryl)-2-chloroacetanilide.

EXAMPLE 23

In this example, a tertiary-2-haloacetamide having N-substituted alkenyl and alkoxyalkyl radicals is prepared using a halomethyl alkyl ether as the alkylating agent.

Three (3) g of N-(3-methyl-2-buten-2-yl)-2-chloroacetamide, 3 ml of chloromethyl ethyl ether and 1.5 gm of triethyl benzyl ammonium chloride were mixed in 100 ml of $CH_2Cl_2$ and cooled to 10° C. Forty (40) ml of 50% NaOH were added all at once and the temperature permitted to rise to room temperature, i.e., 10°–25° C., with stirring. After 30–45 minutes, glc indicated that imidate was present together with the desired tert-amide. The mixture was then treated with HCl to regenerate the above sec-amide and recycled with reduced charge of reactants, i.e., 1.5 ml of chloromethyl ethyl ether, 20 ml caustic soda and 1.0 gm of triethyl benzyl ammonium chloride. On workup (Kugelrohr) 2.7 gm of near colorless oil, b.p. 85°–120° C. at (0.06 mm Hg) having good glc assay was obtained.

Calc'd for $C_{10}H_{18}ClNO_2$ (%): C, 54.67; H, 8.26; N, 6.38 Found: C, 54.41; H, 8.45; N, 6.13

The product was identified as N-(3-methyl-2-buten-2-yl)-N-(ethoxymethyl)-2-chloroacetamide.

EXAMPLE 24

Following essentially the same procedure in Example 23, but substituting 3.0 gm (0.0185 mol) of N(3-methyl-2-N-buten-2yl)-2-chloroacetamide as the sec-amide and 3.3 gm (0.028 mol) of propargyl bromide as the alkylating agent, 2.15 gm (60% yield) of yellow oil, b.p. 109° C. at 0.8 mm Hg (Kugelrohr) was obtained.

Calc'd for $C_{10}H_{14}ClNO$ (%): C, 60.15; H, 7.07; Cl, 17.75 Found: C, 59.96; H, 7.12; Cl, 17.69

The product was identified as N-(3-methyl-2-buten-2yl)-N-2-propynyl-2-chloroacetamide

EXAMPLE 25

This example illustrates the use of the present process to prepare 2-haloacetamides substituted with multiple aliphatic groups on the amide nitrogen atom.

2-Chloroacetamide (4.0 g, 0.042 mol), chloromethyl isobutyl ether (11.0 g, 0.094 mol), benzyl triethyl ammonium chloride (0.6 g) and 100 ml $CH_2Cl_2$ were charged to a 500 ml flask with stirrer. 40 g 50% aqueous NaOH was added all at once, with exotherm to 52° C. After stirring for 0.5 hour, water was added and after separation of layers, the $CH_2Cl_2$ was removed, dried over $MgSO_4$, filtered and solvent removed in vacuo. The residue was taken up in either and washed with water. The ether layer was dried over $MgSO_4$, filtered and solvent removed in vacuo. The residue was vacuum distilled to give 1.0 g of product, b.p. 138°–140° C. at 0.05 mm; yield 9.0%.

Calc'd for $C_{12}H_{24}ClNO_3$ (%): C, 54.23; H, 9.10; N, 5.27 Found: C, 54.03; H, 9.09; N, 5.22

The product was identified as N,N-bis (isobutoxymethyl)-2-chloroacetamide.

EXAMPLE 26

This example illustrates embodiment C of the invention utilizing a metal hydride as the sec-amide anion generator to produce the same t-amide product produced in Example 1.

Potassium hydride (KH) (0.056 mol, 10.2 g.) in mineral oil was washed 3 times with petroleum ether; after each wash most of the solvent was removed through a flexible needle under nitrogen pressure. N-(2,6-dimethyl-1-cyclohexen-1-yl)-2-chloroacetamide (0.05 mol, 11.3 g) in 300 ml ether was added dropwise rapidly with stirring over 0.5 hour, with the theory hydrogen evolved measured by a wet test meter. Freshly-distilled chloromethyl methyl ether (0.18 mol, 15 g) in 200 ml ether was added dropwise and stirred for 50 minutes to insure full precipitation of potassium chloride. Wet ether added cautiously. When all excess KH had reacted, 300 ml of water were added. The ether was extracted, dried over $MgSO_4$, filtered and removed under vacuum leaving 6.3 g of oil which was vacuum distilled to give 4.2 g of oil, b.p. 127° C. (0.15 mm).

EXAMPLE 27

Following the same general procedure described in Example 26, but substituting chloromethyl methyl thioether ($ClCH_2SCH_3$) as the alkylating agent, an oil was obtained in 11% yield.

Calc'd for $C_{12}H_{20}ClNOS$ (%): C, 55.05; H, 7.70; N, 5.35; Found: C, 54.88; H, 7.75; N, 5.29.

The product was identified as N-(methylthiomethyl)-N-(b 2,6-dimethyl-1-cyclohexen-1-yl)-2-chloroacetamide.

In similar manner, when chloromethyl phenyl thioether is used as the alkylating agent, one obtains the corresponding tertiary amide, N-(phenylthiomethyl)-N-(2,6-dimethyl-1-cyclohexen-1-yl)-2-chloroacetamide.

EXAMPLE 28

Following the procedure of the preceding example, 0.05 ml of 2',6'-diethyl-2-chloroacetanilide was reacted with potassium hydride in diethyl ether. The reaction was slow, hence, an ether solution of the anilide, KH and $ClCH_2SCH_3$ was stirred overnight. After completion of the reaction, a water and sodium bicarbonate solution was added. Upon workup, 4.2 g (29% yield) of product, m.p. 42°–49°, was obtained.

Calc'd for $C_{14}H_{20}ClNOS$ (%): C, 58.83; H, 7.05; N, 4.90; Found: C, 58.95; H, 7.09; N, 4.87.

The product was identified as N-(methylthiomethyl)-2'6'-diethyl-2-chloroacetanilide.

In similar manner, when chloromethyl phenyl thioether is used as the alkylating agent, one obtains the corresponding tertiary amide, N-(phenylthiomethyl)-2-chloro-2',6'-diethyl acetanilide.

EXAMPLE 29

In similar manner as described in Example 26, 8.0 gms of (0.04 mol) of 20% KH was reacted with 4.03 gm (0.02 mol) of N-(2,6-dimethyl-1-cyclohexen-1-yl)-2-chloracetamide in diethyl ether solvent to generate the amide anion of the amide, which was then reacted with 6.68 gms (0.04 mol) of methyl 2-bromopropionate. On workup, a white solid, m.p. 85°–95° C. representing a mixture of diasteromers was obtained in 38% yield.

Calc'd for $C_{14}H_{22}ClNO_3$ (%): C, 58.43; H, 7.71; N, 4.87 Found: C, 58.42; H, 7.75; N, 4.93

The product was identified as N-(1-methoxycarbonyl-1-ethyl)-N-(2,6-dimethyl-1-cyclohexen-1-yl)-2-chloroacetamide.

EXAMPLE 30

Following the general procedure described in Example 26, but substituting ethyl 2-bromopropionate as the alkylating agent, a white solid, m.p. 50°–60° C., representing a mixture of diastereomers, was obtained in 28% yield.

Calc'd for $C_{15}H_{24}ClNO_3$ (%): C, 59.69; H, 8.02; N, 4.64 Found: C, 59.85; H, 8.06; N, 4.62

The product was identified as N-(1-ethoxycarbonyl-1-ethyl)-N-(2,6-dimethyl-1-cyclohexen-1-yl)-2-chloroacetamide.

EXAMPLE 31

In this example 2'6'-dimethyl-2-chloroacetanilide (0.05 mol) was dissolved in tetrahydrofuran (THF) and reacted with KH, the reaction in this solvent was quite rapid. $CH_3SCH_2Cl$ was then added as above and stirred for about two hours at 35°–40° C. The product was washed with $NaHCO_3$ and identified as N-(methylthiomethyl)-2',6'-dimethyl-2-chloroacetanilide.

EXAMPLE 32

Potassium hydride (0.056 mol) in petroleum ether and N-(2,6-dimethyl-1-cyclohexen-1-yl)-2-chloroacetamide (0.05 mol) dissolved in 300 ml of ether were mixed and refluxed at 30° with evolution of about 2–2.5 l of gas 0.085 mol of freshly prepared 1-chloroethyl methyl ether

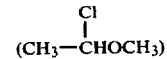

was added with stirring (strong exotherm) over a 15 minute period with precipitation of a white solid. On workup, a solid was obtained in 23% yield, m.p. 76°–79° C.

Calc'd for $C_{13}H_{22}ClNO_2$ (%): C, 60.11; H, 8.54; N, 5.39; Found: C, 59.96; H, 8.57; N, 5.44.

The product was identified as N-(1-methoxy-1-ethyl)-N-(2,6-dimethyl-1-cyclohexen-1yl)-2-chloroacetamide.

EXAMPLE 33

The same general procedure of Example 32 was followed, except here the sec-amide, 2'-methyl-6'-ethyl-2-chloroacetanilide, 21.1 g (0.1 mol), was solubilized with a small amount of THF in 400–500 ml diethyl ether. Reaction went well, but gas evolved when chloroethyl methyl ether was added. However, at final addition (about 2.5×theory) the added ether didn't react although some KH was still present. Upon workup, the product, N-(1-methoxy-1-ethyl)-2'-methyl-6'-ethyl-2-chloroacetanilide, was obtained in 86% yield, b.p. 130° at 0.05 mm Hg.

Calc'd for $C_{14}H_{20}ClNO_2$ (%): C, 62.33; H, 7.47; N, 5.19; Found: C, 62.37; H, 7.47; N, 5.19.

EXAMPLE 34

Following the procedure of Example 33 except using the sec-amide 2',6'-diethyl-2-chloroacetanilide, the corresponding tertiary amide, N-(1-methoxy-1-ethyl)-2',6'-diethyl-2-chloroacetanilide, was prepared. The product, b.p. 153°/0.05, was obtained in 41% yield.

Calc'd for $C_{15}H_{22}ClNO_2$ (%): C, 63.48; H, 7.81; N, 4.94; Found: C, 63.46; H, 7.84; N, 4.91.

EXAMPLE 35

Twenty (20) mol of 20–25% KH slurry (ca. 0.05 mol) washed 4 times with ca 300 ml petroleum ether each time. Last was permitted to stand overnight, then diethyl ether added, stirring started and 10 g of N-(2,6-dimethyl-1-cyclohexen-1-yl)-2-chloroacetamide dissolved in 400 ml ether added thereto with continued stirring. Hydrogen allowed to exit through wet test meter (1.5 l evolved); then 10 g. (0.072 mol) 2-bromoethyl methyl ether was added. Mixture refluxed for 4 hours, then stirred overnight at room temperature. Upon work-up 3.5 g distilled yield was obtained; b.p. 160°–190°/0.04 mm.

Calc'd for $C_{13}H_{22}ClNO_2$ (%): N, 5.39; Cl, 13.65 Found: N, 5.71; Cl, 13.95

Product verified by GLC was identified as N-(2-methoxyethyl)-N-(2,6-dimethyl-1-cyclohexen-1-yl)-2-chloroacetanilide.

EXAMPLE 36

This example illustrates sec-amide anion formation by direct electrochemical reduction and alkylation of the anion (Embodiment D).

The electrolyses were performed in an all-glass H-cell of conventional design with a sodium porosity sintered glass frit separating the anode and cathode compartments. The volume of the cathode compartment was approximately 70 ml and that of the anode compartment was approximately 30 ml. The cathode was a 45-mesh platinum gauze rectangle with a geometrical area of approximately 12 $cm^2$. The anode was a graphite rod with a diameter of 6 mm. A silver wire reference electrode extended into the cathode compartment and was contained and separated from the catholyte by a fritted compartment.

The solvent may be acetonitrile, N,N-dimethylformamide or other aprotic dipolar solvents suitable for electrochemical reductions which contain a sufficient concentration of a supporting electrolyte salt to render it sufficiently conducting. The supporting electrolytes include, but are not limited to, alkali metal perchlorates, fluoborates and halides and tetraalkylammonium perchlorates, fluoborates and halides.

The solvent-supporting electrolyte mixture was charged into both the cathode and anode compartments, and the catholyte was purged with an inert gas such as nitrogen or argon to remove dissolved oxygen. To the catholyte was added the secondary α-chloroacetamide and the electrolysis was initiated. The electrolysis was carried out in a controlled potential mode using a Princeton Applied Research Model 173 potentiostat. The cathode potential relative to the silver reference electrode was maintained sufficiently negative to reduce the amide, as evidenced by hydrogen evolution at the cathode. Upon completion of the electrolysis, a chloromethyl alkyl ether was added to alkyate the amide anion generated during the electrolysis. The chloromethyl ether may not be present in significant concentrations during the electrolysis since it is reduced in preference to the amide. In cases where alkylation of the amide anion by neutral α-chloroacetamide is a problem, the yield of desired product may be improved by adding the alkylating agent during the electrolysis in proportion to the amount of current passed.

As a specific example, 0.40 gram of N-(2,6-dimethyl-1-cyclohexen-1-yl)-2-chloroacetamide (the product of Example 1(a)) was electrolyzed in in acetonitrile which was 0.1 M in sodium perchlorate. The cathode potential was maintained at −2.0 V vs. the Ag reference electrode. After passing 193 coulombs, 0.21 g. of chloromethyl ethyl ether was added to the catholyte and allowed to stir for one-half (½) hour.

The catholyte was separated, and most of the acetonitrile was removed under reduced pressure. Water was added to the residue, and the aqueous solution was extracted with 150 ml of ethyl ether. The ether solution was washed with water and saturated sodium chloride solution and dried over anhydrous magnesium sulfate. The mixture was filtered and ether was removed from the filtrate under reduced pressure to yield a clear oil. Gas chromatographic analysis of the reaction mixture indicates 16% secondary amide, 36.5% desired tertiary amide, N-(2',6'-dimethyl-1-cyclohexen-1-yl)-N-(ethoxymethyl)-2-chloroacetamide, and 44% N,N'-bis(2,6-dimethyl-1-cyclohexenyl)piperazine-2,5-dione, the product resulting from self-alkylation. Optimization of this procedure would increase yield of tert-amide product and decrease undesired by-products.

EXAMPLE 37–176

Following the same general processes described in Examples 1–36, but substituting the appropriate starting materials and reaction conditions, other exemplary tertiary 2-haloacetamide compounds according to Formula I above are prepared from the corresponding sec-amide and the same or equivalent anion generators, alkylating agents, solvents and/or phase-transfer catalysts. Typical of such compounds which are prepared according to the process of this invention are shown in the following table together with certain of their physical properties.

TABLE I

| Example No. | Compound | Empirical Formula | B.P. °C. (mm Hg) | Element | Analysis Calculated | Found |
|---|---|---|---|---|---|---|
| 37 | N-(methoxymethyl)-N-(2-methyl-1-cyclohexen-1-yl)-2-chloroacetamide | $C_{11}H_{18}ClNO_2$ | 29–31 (m.p) | C<br>H<br>N | 57.02<br>7.83<br>6.04 | 56.86<br>7.86<br>5.96 |
| 38 | N-(isobutoxymethyl)-N-(2,6-dimethyl-1-cyclohexen-1-yl)-2-chloroacetamide | $C_{15}H_{26}ClNO_2$ | 120 (0.1) | C<br>H<br>N | 62.59<br>9.10<br>4.87 | 62.33<br>9.16<br>4.78 |
| 39 | N-(butoxymethyl)-N-(2,6-dimethyl-1-cyclohexen-1-yl)-2-chloroacetamide | $C_{15}H_{26}ClNO_2$ | 132 (0.05) | C<br>H<br>N | 62.59<br>12.33<br>4.87 | 62.39<br>12.16<br>4.95 |
| 40 | N-(methoxymethyl)-N-(2-sec-butyl-1-cyclohexen-1-yl)-2-chloroacetamide | $C_{14}H_{24}ClNO_2$ | 125 (0.05) | C<br>H<br>N | 61.41<br>8.84<br>5.12 | 61.52<br>8.86<br>5.11 |
| 41 | N-(propoxymethyl)-N-(2,6-dimethyl-1-cyclohexen-1-yl)-2-chloroacetamide | $C_{14}H_{24}ClNO_2$ | 115 (0.05) | C<br>H<br>N | 61.41<br>8.84<br>5.12 | 61.51<br>8.84<br>5.18 |
| 42 | N-(methoxymethyl)-N-(2-ethyl-1-cyclohexen-1-yl)-2-chloroacetamide | $C_{12}H_{20}ClNO_2$ | 117 (0.05) | C<br>H<br>N | 58.65<br>8.20<br>5.70 | 58.75<br>8.29<br>5.66 |
| 43 | N-(allyloxymethyl)-N-(2,6-dimethyl-1-cyclohexen-1-yl)-2-chloroacetamide | $C_{14}H_{22}ClNO_2$ | 129 (0.05) | C<br>H<br>N | 61.87<br>8.16<br>5.15 | 61.69<br>8.19<br>5.12 |
| 44 | N-(isopropoxymethyl)-N-(2,6-dimethyl-1-cyclohexen-1-yl)-2-chloroacetamide | $C_{14}H_{24}ClNO_2$ | 115 (0.05) | C<br>H<br>N | 61.41<br>8.84<br>5.12 | 61.24<br>8.86<br>5.10 |
| 45 | N-(propargyloxymethyl)-N-(2,6-dimethyl-1-cyclohexen-1-yl)-2-chloroacetamide | $C_{14}H_{20}ClNO_2$ | 150 (0.05) | C<br>H<br>N | 62.53<br>7.47<br>5.79 | 62.33<br>7.48<br>5.75 |
| 46 | N-(sec-butoxymethyl)-N-(2,6-dimethyl-1-cyclohexen-1-yl)-2-chloroacetamide | $C_{15}H_{26}ClNO_2$ | 133 (0.05) | C<br>H<br>N | 62.59<br>9.10<br>4.87 | 62.44<br>9.13<br>4.82 |
| 47 | N-(2-chloro-1-ethoxymethyl)-N-(2,6-dimethyl-1-cyclohexen-1-yl)-2-chloroacetamide | $C_{13}H_{21}Cl_2NO_2$ | 150 (0.05) | C<br>H<br>N | 53.07<br>7.19<br>4.76 | 52.94<br>7.25<br>4.68 |
| 48 | N-(2-buten-1-oxymethyl)-N-(2,6-dimethyl-1-cyclohexen-1-yl)-2-chloroacetamide | $C_{16}H_{22}ClNO$ | 111–113 (m.p.) | C<br>H<br>N | 63.04<br>8.46<br>4.90 | 62.86<br>8.54<br>4.81 |
| 49 | N-(t-butoxymethyl)-N-(2,6-dimethyl-1-cyclohexen-1-yl)-2-chloroacetamide | $C_{15}H_{26}ClNO_2$ | 120 (0.05) | C<br>H<br>N | 62.59<br>9.10<br>4.87 | 62.38<br>9.10<br>4.83 |
| 50 | N-(methoxymethyl)-N-(2-isopropyl-1-cyclohexen-1-yl)-2-chloroacetamide | $C_{13}H_{22}ClNO_2$ | 120 (0.05) | C<br>H<br>N | 60.11<br>8.54<br>5.39 | 60.43<br>8.71<br>5.15 |
| 51 | N-(propoxymethyl)-N-[2-(1-methylpropyl)-1-cyclohexen-1-yl]-2-chloroacetamide | $C_{16}H_{28}ClNO_2$ | 136 (0.05) | C<br>H<br>N | 63.66<br>9.35<br>4.64 | 63.75<br>9.42<br>4.61 |
| 52 | N-(allyloxymethyl)-N-(2-ethyl-1-cyclohexen-1-yl)-2-chloroacetamide | $C_{14}H_{22}ClNO_2$ | 124 (0.05) | C<br>H<br>N | 61.87<br>8.16<br>5.15 | 61.88<br>8.17<br>5.15 |
| 53 | N-(ethoxyethoxymethyl)-N-(2,6-dimethyl-1-cyclohexen-1-yl)-2-chloroacetamide | $C_{15}H_{26}ClNO_3$ | | C<br>H<br>N | 59.30<br>8.63<br>4.61 | 59.20<br>8.63<br>4.61 |
| 54 | N-(butoxymethyl)-N-(2-methyl-1-cyclohexen-1-yl)-2-chloroacetamide | $C_{14}H_{24}ClNO_2$ | 132 (0.05) | C<br>H<br>N | 61.41<br>8.81<br>5.12 | 62.43<br>9.12<br>5.85 |
| 55 | N-(methoxyethoxymethyl)-(2,6-dimethyl-1-cyclohexen-1-yl)-2-chloroacetamide | $C_{14}H_{24}ClNO_3$ | 140 (0.05) | C<br>H<br>N | 58.02<br>8.35<br>4.83 | 57.84<br>8.41<br>4.80 |
| 56 | N-(3,3-dichloro-2-propenoxymethyl)-N-(2,6-dimethyl-1-cyclohexen-1-yl)-2-chloroacetamide | $C_{14}H_{20}Cl_3NO_2$ | 173 (0.25) | C<br>H<br>N | 49.36<br>5.92<br>4.11 | 49.17<br>5.95<br>4.09 |
| 57 | N-(3-chloro-2-propenoxymethyl)-N-(2,6-dimethyl-1-cyclohexen-1-yl)-2-chloroacetamide | $C_{14}H_{20}Cl_2NO_2$ | 159 (0.05) | C<br>H<br>N | 54.91<br>6.91<br>4.57 | 54.91<br>6.91<br>4.56 |
| 58 | N-(2,3,-trichloro-2-propenoxymethyl)-N-(2,6-dimethyl-1-cyclohexen-1-yl)-2-chloroacetamide | $C_{14}H_{19}Cl_4NO_2$ | 173 (0.1) | C<br>H<br>N | 44.83<br>5.11<br>3.73 | 44.78<br>5.14<br>3.71 |
| 59 | N-(2,3-dichloro-2-propenoxymethyl)-N-(2,6-dimethyl-1-cyclohexen-1-yl)-2-chloroacetamide | $C_{14}H_{20}Cl_3NO_2$ | 166 (0.05) | C<br>H<br>N | 49.36<br>5.92<br>4.11 | 49.69<br>6.28<br>4.13 |
| 60 | N-(2-chloro-2-propenoxymethyl)-N-(2,6-dimethyl-1-cyclohexen-1-yl)-2-chloroacetamide | $C_{19}H_{21}Cl_2NO_2$ | 159 (.025) | C<br>H<br>N | 54.91<br>6.91<br>4.57 | 54.86<br>6.92<br>4.56 |
| 61 | N-(isobutoxymethyl)-N-(1-cyclohexen-1-yl)-2-chloroacetamide | $C_{13}H_{22}ClNO_2$ | 120 (0.05) | C<br>H<br>N | 60.11<br>8.54<br>5.39 | 59.98<br>8.55<br>5.38 |
| 62 | N-(methallyloxymethyl)-N-(2,6-dimethyl-1-cyclohexen- | $C_{15}H_{24}ClNO_2$ | 128 (0.05) | C<br>H | 63.04<br>8.46 | 62.89<br>8.45 |

TABLE I-continued

| Example No. | Compound | Empirical Formula | B.P. °C. (mm Hg) | Element | Analysis Calculated | Found |
|---|---|---|---|---|---|---|
| | 1-yl)-2-chloroacetamide | | | N | 4.90 | 4.83 |
| 63 | N-(2-propynyl)-N-(2,6-dimethyl-1-cyclohexen-1-yl)-2-chloroacetamide | $C_{13}H_{18}ClNO$ | 125 (0.05) | C H N | 65.13 7.57 5.84 | 63.68 7.43 5.65 |
| 64 | N-(methoxymethyl)-N-(2,6-diethyl-1-cyclohexen-1-yl)-2-chloroacetamide | $C_{14}H_{24}ClNO_2$ | 150 (0.05) | C H N | 61.41 8.84 5.12 | 61.42 8.87 5.09 |
| 65 | N-(ethoxymethyl)-N-(2,6-diethyl-1-cyclohexen-1-yl)-2-chloroacetamide | $C_{15}H_{26}ClNO_2$ | 150 (0.05) | C H N | 62.59 9.11 4.87 | 62.44 9.10 4.82 |
| 66 | N-(ethoxymethyl)-N-(2-ethyl-6-t-butyl-1-cyclohexen-1-yl)-2-chloroacetamide | $C_{16}H_{28}ClNO_2$ | 140 (0.05) | C H N | 63.66 9.35 4.64 | 63.47 9.35 4.60 |
| 67 | N-(ethoxymethyl)-N-(2-isopropyl-1-cyclohexen-1-yl)-2-chloroacetamide | $C_{14}H_{24}ClNO_2$ | 126 (0.05) | C H N | 61.41 8.84 5.12 | 61.25 8.87 5.11 |
| 68 | N-(methoxymethyl)-N-(2-methyl-6-ethyl-1-cyclohexen-1-yl)-2-chloroacetamide | $C_{13}H_{22}ClNO_2$ | 130 (0.05) | C H N | 60.11 8.54 5.39 | 60.00 8.57 5.33 |
| 69 | N-(methoxymethyl)-N-(2-ethyl-6-methyl-1-cyclohexen-1-yl)-2-chloroacetamide | $C_{13}H_{22}ClNO_2$ | 130 (0.05) | C H N | 60.11 8.54 5.39 | 60.08 8.54 5.39 |
| 70 | N-(ethoxymethyl)-N-(2-ethyl-1-cyclohexen-1-yl)-2-chloroacetamide | $C_{13}H_{22}ClNO_2$ | 125 (0.05) | C H N | 60.11 8.54 5.39 | 59.92 8.63 5.31 |
| 71 | N-(methoxymethyl)-N-(2-t-butyl-1-cyclohexen-1-yl)-2-chloroacetamide | $C_{14}H_{24}ClNO_2$ | 130 (0.05) | C H N | 61.41 8.84 5.12 | 60.60 8.82 4.86 |
| 72 | N-(methoxymethyl)-N-(6-t-butyl-1-cyclohexen-1-yl)-2-chloroacetamide | $C_{14}H_{24}ClNO_2$ | 130 (0.05) | C H N | 61.41 8.84 5.12 | 61.08 8.74 4.90 |
| 73 | N-(ethoxymethyl)-N-(2-ethyl-6-methyl-1-cyclohexen-1-yl)-2-chloroacetamide | $C_{14}H_{22}ClNO_2$ | 123 (0.05) | C H N | 61.42 8.84 5.12 | 61.38 8.84 5.07 |
| 74 | N-(ethoxymethyl)-N-(2-methyl-6-ethyl-1-cyclohexen-1-yl)-2-chloroacetamide | $C_{14}H_{22}ClNO_2$ | 125 (0.05) | C H N | 61.42 8.84 5.12 | 61.38 8.84 5.07 |
| 75 | N-(ethoxymethyl)-N-(2,5-dimethyl-1-cyclopenten-1-yl)-2-chloroacetamide | $C_{12}H_{20}ClNO_2$ | 137 (0.05) | C H N | 58.65 8.20 5.70 | 59.17 8.37 5.43 |
| 76 | N-(n-propoxymethyl)-N-(2,5-dimethyl-1-cyclopenten-1-yl)-2-chloroacetamide | $C_{13}H_{22}ClNO_2$ | 140 (0.05) | C H N | 60.11 8.54 5.39 | 59.21 8.56 5.10 |
| 77 | N-(methoxymethyl)-N-(2-isopropyl-6-methyl-1-cyclohexen-1-yl)-2-chloroacetamide | $C_{14}H_{24}ClNO_2$ | 140 (0.05) | C H N | 61.41 8.84 5.12 | 61.04 8.93 4.90 |
| 78 | N-(methoxymethyl)-N-(2-methyl-6-isopropyl-1-cyclohexen-1-yl)-2-chloroacetamide | $C_{14}H_{24}ClNO_2$ | — | C H N | 61.41 8.84 5.12 | 61.08 8.93 4.88 |
| 79 | N-(2-cyano-2-propoxymethyl)-N-(2,6-dimethyl-1-cyclohexen-1-yl)-2-chloroacetamide | $C_{15}H_{23}ClNO_2$ | 140 (0.05) | C H N | 60.29 7.76 9.38 | 60.29 7.76 9.37 |
| 80 | N-(cyclopropylmethoxymethyl)-N-(2,6-dimethyl-1-cyclohexen-1-yl)-2-chloroacetamide | $C_{15}H_{24}ClNO_2$ | 130 (0.05) | C H N | 63.04 8.46 4.90 | 63.02 8.50 4.91 |
| 81 | N-(sec-butoxymethyl)-N-(2,6-diethyl-1-cyclohexen-1-yl)-2-chloroacetamide | $C_{17}H_{30}ClNO_2$ | 156 (0.05) | C H N | 64.64 9.57 4.43 | 64.53 9.60 4.43 |
| 82 | N-(allyloxymethyl)-N-(2,6-diethyl-1-cyclohexen-1-yl)-2-chloroacetamide | $C_{16}H_{26}ClNO_2$ | 133 (0.05) | C H N | 64.09 8.74 4.67 | 63.91 8.74 4.64 |
| 83 | N-(propargyloxymethyl)-N-(2,6-diethyl-1-cyclohexen-1-yl)-2-chloroacetamide | $C_{16}H_{24}ClNO_2$ | 146 (0.05) | C H N | 64.55 8.12 4.70 | 64.53 8.12 4.70 |
| 84 | N-(methoxyethoxymethyl)-N-(2,6-diethyl-1-cyclohexen-1-yl)-2-chloroacetamide | $C_{16}H_{28}ClNO_3$ | 160 (0.05) | C H N | 60.46 8.88 4.41 | 60.28 8.87 4.39 |
| 85 | N-(2-methyl-2-propen-1-oxymethyl)-N-(2,6-diethyl-1-cyclohexen-1-yl)-2-chloroacetamide | $C_{17}H_{28}ClNO_2$ | 140 (0.05) | C H N | 65.06 8.99 4.46 | 64.93 9.00 4.43 |
| 86 | N-(n-propoxymethyl)-N-(2,6-diethyl-1-cyclohexen-1-yl)-2-chloroacetamide | $C_{16}H_{28}ClNO_2$ | 140 (0.05) | C H N | 63.66 9.35 4.64 | 63.61 9.35 4.62 |
| 87 | N-(2-methyl-1-propoxymethyl)-N-(2,6-diethyl-1-cyclohexen-1-yl)-2-chloroacetamide | $C_{17}H_{30}ClNO_2$ | 137 (0.05) | C H N | 64.64 9.57 4.43 | 64.50 9.63 4.39 |
| 88 | N-(1-methylethoxymethyl)-N-(2,6-diethyl-1-cyclohexen-1-yl)-2-chloroacetamide | $C_{16}H_{28}ClNO_2$ | 134 (0.05) | C H N | 63.66 9.35 4.64 | 63.50 9.36 4.65 |

TABLE I-continued

| Example No. | Compound | Empirical Formula | B.P. °C. (mm Hg) | Element | Analysis Calculated | Found |
|---|---|---|---|---|---|---|
| 89 | N-(n-butoxymethyl)-N-(2,6-diethyl-1-cyclohexen-1-yl)-2-chloroacetamide | $C_{17}H_{30}ClNO_2$ | 155 (0.05) | C<br>H<br>N | 64.64<br>9.57<br>4.43 | 64.58<br>9.59<br>4.44 |
| 90 | N-(1,1-dimethylethoxymethyl)-N-(2,6-diethyl-1-cyclohexen-1-yl)-2-chloroacetamide | $C_{17}H_{30}ClNO_2$ | 142 (0.05) | C<br>H<br>N | 64.64<br>9.57<br>4.43 | 64.61<br>9.58<br>4.43 |
| 91 | N-(1-methylpropoxymethyl)-N-(2-methyl-1-cyclohexen-1-yl)-2-chloroacetamide | $C_{14}H_{25}ClNO_2$ | 116 (0.05) | C<br>H<br>N | 61.41<br>8.84<br>5.12 | 61.38<br>8.85<br>5.09 |
| 92 | N-(n-propoxymethyl)-N-(2-methyl-1-cyclohexen-1-yl)-2-chloroacetamide | $C_{13}H_{22}ClNO_2$ | 119 (0.05) | C<br>H<br>N | 60.11<br>8.54<br>5.39 | 60.23<br>8.62<br>5.37 |
| 93 | N-(1-methylethoxymethyl)-N-(2-methyl-1-cyclohexen-1-yl)-2-chloroacetamide | $C_{13}H_{22}ClNO_2$ | 107 (0.05) | C<br>H<br>N | 60.11<br>8.54<br>5.39 | 60.02<br>8.58<br>5.35 |
| 94 | N-(2-propenoxymethyl)-N-(2-methylethyl-1-cyclohexen-1-yl)-2-chloroacetamide | $C_{15}H_{24}ClNO_2$ | 130 (0.05) | C<br>H<br>N | 63.04<br>8.46<br>4.90 | 63.11<br>8.50<br>4.89 |
| 95 | N-(2-propenoxymethyl)-N-(2-methyl-6-ethyl-1-cyclohexen-1-yl)-2-chloracetamide | $C_{15}H_{24}ClNO_2$ | 130 (0.05) | C<br>H<br>N | 63.04<br>8.46<br>4.90 | 62.90<br>8.45<br>4.82 |
| 96 | N-(2-propenoxymethyl)-N-(2-methyl-1-cyclohexen-1-yl)-2-chloroacetamide | $C_{13}H_{20}ClNO_2$ | 124 (0.05) | C<br>H<br>N | 60.58<br>7.82<br>5.43 | 60.54<br>7.83<br>5.41 |
| 97 | N-(ethoxymethyl)-N-(2-methyl-1-cyclohexen-1-yl)-2-chloroacetamide | $C_{12}H_{20}ClNO_2$ | 122 (0.05) | C<br>H<br>N | 58.65<br>8.20<br>5.70 | 58.92<br>7.80<br>5.61 |
| 98 | N-(methoxymethyl)-2'-t-butyl-6'-(2-methoxyethyl)-2-chloroacetanilide | $C_{17}H_{26}ClNO_3$ | 185–195 (0.15–0.2) | C<br>H<br>N | 62.28<br>7.99<br>4.27 | 62.80<br>8.01<br>4.08 |
| 99 | N-[N'-(methoxymethyl) acetamidomethyl]-2',6'-diethyl-2-chloroacetanilide | $C_{17}H_{25}ClNO_3$ | Oil | C<br>H<br>N | 59.91<br>7.39<br>8.22 | 59.41<br>7.45<br>7.86 |
| 100 | N-(methoxymethyl)-2',6'-dinitro-2-chloroacetanilide | $C_{10}H_{10}ClN_3O_6$ | 105.5–108 (m.p.) | C<br>H<br>N | 39.55<br>3.32<br>13.84 | 39.42<br>3.22<br>14.22 |
| 101 | N-(methoxymethyl)-2,2',6'-trichloroacetanilide | $C_{10}H_{10}Cl_3NO_2$ | 137 (0.025) | C<br>H<br>N | 42.51<br>3.57<br>4.96 | 42.62<br>3.61<br>4.99 |
| 102 | N-(ethoxymethyl)-2',6'-dimethoxy-2-chloroacetanilide | $C_{13}H_{18}ClNO_4$ | 95–97 (m.p.) | C<br>H<br>N | 54.26<br>6.31<br>4.87 | 54.22<br>6.34<br>4.86 |
| 103 | N-(1-methoxy-1-ethyl)-2',6'-diethyl-2-chloroacetanilide | $C_{15}H_{22}ClNO_2$ | 153 (0.05) | C<br>H<br>N | 63.48<br>7.81<br>4.94 | 63.46<br>7.84<br>4.91 |
| 104 | N-(1-methoxy-1-ethyl)-2-2'-methyl-6'-t-butyl-2-chloroacetanilide | $C_{16}H_{24}ClNO_2$ | 108–109 (m.p.) | C<br>H<br>N | 64.53<br>8.12<br>4.70 | 64.54<br>8.13<br>4.72 |
| 105 | N-(ethoxymethyl)-2'-(2,6-dimethylphenoxy)-2-chloroacetanilide | $C_{19}H_{22}ClNO_3$ | 105–107 (m.p.) | C<br>H<br>Cl<br>N | 65.61<br>6.38<br>10.19<br>4.03 | 65.58<br>6.44<br>10.18<br>4.03 |
| 106 | N-(methoxymethyl)-4'-(2,6-diisopropylphenyl)-2-chloroacetanilide | $C_{22}H_{28}ClNO_3$ | 103–105 (m.p.) | C<br>H<br>Cl<br>N | 67.77<br>7.24<br>9.09<br>3.59 | 67.56<br>7.29<br>9.07<br>3.58 |
| 107 | N-(methoxymethyl)-2'-(2,6-dichlorophenoxy)-2-chloroacetanilide | $C_{16}H_{14}Cl_3NO_3$ | 118–120 (m.p.) | C<br>H<br>Cl<br>N | 51.29<br>3.77<br>28.39<br>3.74 | 51.20<br>3.77<br>28.38<br>3.72 |
| 108 | N-(cylopropylmethoxymethyl)-2'-methoxy-6'-methyl-2-chloroacetanilide | $C_{15}H_{20}ClNO_3$ | 145° (oil) | C<br>H<br>N | 60.50<br>6.77<br>4.70 | 60.26<br>6.77<br>4.66 |
| 109 | N-(methoxymethyl)-2'-methyl-6'-methoxymethyl-2-chloroacetanilide | $C_{13}H_{18}ClNO_3$ | 180 (0.05) | C<br>H<br>N | 57.46<br>6.68<br>5.15 | 57.32<br>6.72<br>5.13 |
| 110 | N-(n-butoxymethyl)-2'-methyl-6'-methoxymethyl-2-chloroacetanilide | $C_{16}H_{24}ClNO_3$ | Oil | C<br>H<br>N | 61.24<br>7.71<br>4.46 | 62.12<br>8.01<br>4.29 |
| 111 | N-(ethoxymethyl)-2'-methyl-6'-methoxymethyl-2-chloroacetanilide | $C_{14}H_{20}ClNO_3$ | Oil | C<br>H<br>N | 58.84<br>7.05<br>4.90 | 59.86<br>7.14<br>4.94 |
| 112 | N-(ethoxymethyl)-2'-t-butyl-6'-ethenyl-2-chloroacetanilide | $C_{17}H_{24}ClNO_2$ | 170–180 (0.025) | C<br>H<br>N | 65.90<br>7.81<br>4.52 | 65.84<br>7.84<br>4.52 |
| 113 | N-(2-propenoxymethyl)-2'-methyl-6'-t-butyl-2-chloroacetanilide | $C_{17}H_{24}ClNO_2$ | 150 (0.05) | C<br>H<br>N | 65.90<br>7.81<br>4.52 | 65.79<br>7.82<br>4.51 |
| 114 | N-(2-propenoxymethyl)-2',6'-dimethyl-2-bromoacetanilide | $C_{14}H_{18}BrNO_2$ | 157 (0.05) | C<br>H | —<br>— | —<br>— |

TABLE I-continued

| Example No. | Compound | Empirical Formula | B.P. °C. (mm Hg) | Element | Analysis Calculated | Found |
|---|---|---|---|---|---|---|
| 115 | N-(methoxymethyl)-N-(1-cyclohexen-1-yl)-2-chloroacetamide | $C_{10}H_{16}ClNO_2$ | — | N<br>C<br>H | —<br>—<br>— | —<br>—<br>— |
| 116 | N-(n-propoxymethyl)-2'-methoxy-6'-methyl-2-chloroacetanilide | $C_{14}H_{20}ClNO_3$ | — | N<br>C<br>H<br>N | —<br>58.84<br>7.05<br>4.90 | —<br>59.04<br>7.22<br>4.87 |
| 117 | N-(allyloxymethyl)-2'-ethoxy-2-chloroacetanilide | $C_{14}H_{18}ClNO_3$ | 134 | C<br>H<br>N | 59.26<br>6.39<br>4.94 | 59.20<br>6.41<br>4.95 |
| 118 | N-(isopropoxymethyl)-2'-methoxy-6'-ethyl-2-chloroacetanilide | $C_{15}H_{22}ClNO_3$ | — | C<br>H<br>N | 60.10<br>7.40<br>4.67 | 59.81<br>7.46<br>4.61 |
| 119 | N-(sec-butoxymethyl)-2'-methoxy-6'-methyl-2-chloroacetanilide | $C_{15}H_{22}ClNO_3$ | 140 (Oil) | C<br>H<br>N | 60.10<br>7.40<br>4.67 | 59.88<br>7.41<br>4.62 |
| 120 | N-(isopropoxymethyl)-2'-methoxy-6'-methyl-2-chloroacetanilide | $C_{14}H_{20}ClNO_3$ | 40-41 (m.p.) | C<br>H<br>N<br>Cl | 58.84<br>7.05<br>4.90<br>12.41 | 58.55<br>7.08<br>4.89<br>12.45 |
| 121 | N-(ethoxymethyl)-2'-isopropoxy-6'-methyl 2-chloroacetanilide | $C_{15}H_{22}ClNO_3$ | — | C<br>H<br>N<br>Cl | 60.10<br>7.40<br>4.67<br>11.83 | 60.10<br>7.40<br>4.64<br>11.73 |
| 122 | N-(n-propoxymethyl)-2'-isopropoxy-6'-methyl-2-chloroacetanilide | $C_{16}H_{24}ClNO_3$ | — | C<br>H<br>N<br>Cl | 61.24<br>7.71<br>4.46<br>11.30 | 61.18<br>7.76<br>4.43<br>11.31 |
| 123 | N-(ethoxymethyl)-2'-n-propoxy-6'-methyl-2-chloroacatanilide | $C_{15}H_{22}ClNO_3$ | 130 (0.07) | C<br>H<br>Cl | 60.10<br>7.40<br>11.83 | 59.95<br>7.39<br>11.79 |
| 124 | N-(ethoxymethyl)-2'-methoxy-6'-methyl-2-chloroacetanilide | $C_{13}H_{18}ClNO_3$ | 170 (0.1) | C<br>H<br>N<br>Cl | 57.46<br>6.67<br>5.16<br>13.05 | 57.19<br>6.70<br>5.11<br>13.09 |
| 125 | N-(1-methylpropoxymethyl)-2'-methoxy-6'-methyl-2-chloroacetanilide | $C_{15}H_{22}ClNO_3$ | — | C<br>H<br>N<br>Cl | 60.10<br>7.40<br>4.67<br>11.83 | 59.90<br>7.36<br>4.62<br>11.97 |
| 126 | N-(allyloxymethyl)-2'-ethoxy-6'-methyl-2-chloroacetanilide | $C_{10}H_{20}ClNO_3$ | 110 (0.07) | C<br>H<br>N<br>Cl | 60.50<br>6.77<br>4.70<br>11.91 | 60.30<br>6.80<br>4.64<br>11.69 |
| 127 | N-(propargyloxymethyl)-2'-ethoxy-6'-methyl-2-chloroacetanilide | $C_{15}H_{18}ClNO_3$ | 140 (0.1) | C<br>H<br>N<br>Cl | 60.91<br>6.13<br>4.74<br>11.99 | 60.98<br>6.14<br>4.74<br>11.94 |
| 128 | N-(1-methylpropoxymethyl)-2'-ethoxy-6'-methyl-2-chloroacetanilide | $C_{16}H_{24}ClNO_3$ | 135 (0.09) | C<br>H<br>N<br>Cl | 61.24<br>7.71<br>4.46<br>11.30 | 60.98<br>7.69<br>4.42<br>11.22 |
| 129 | N-(n-propoxymethyl)-2'-isobutoxy-6'-methyl-2-chloroacetanilide | $C_{17}H_{26}ClNO_3$ | 130 (0.04) | C<br>H<br>Cl | 62.28<br>7.99<br>10.81 | 62.27<br>8.01<br>10.81 |
| 130 | N-(ethoxymethyl)-2'-n-butoxy-6'-isopropyl-2-chloroacetanilide | $C_{18}H_{28}ClNO_3$ | 125 (0.07) | C<br>H<br>Cl | 63.24<br>8.26<br>10.37 | 63.23<br>8.29<br>10.37 |
| 131 | N-(isobutoxymethyl)-2'-isobutoxy-6'methyl-2-chloroacetanilide | $C_{18}H_{28}ClNO_3$ | 115 (0.02) | C<br>H<br>Cl | 63.24<br>8.26<br>10.37 | 63.19<br>8.30<br>10.38 |
| 132 | N-(isopropoxymethyl)-2'-isobutoxy-6'-methyl-2-chloroacetanilide | $C_{17}H_{26}ClNO_3$ | 120 (0.03) | C<br>H<br>Cl | 62.28<br>7.99<br>10.81 | 62.26<br>7.99<br>10.81 |
| 133 | N-(2-buten-1-oxymethyl)-2'-methoxy-6'-methyl-2-chloroacetanilide | $C_{15}H_{20}ClNO_3$ | 114 (0.03) | C<br>H<br>Cl | 60.50<br>6.77<br>11.91 | 60.38<br>6.83<br>11.85 |
| 134 | N-(isobutoxymethyl)-2'-isoproxy-6'-methyl-2-chloroacetanilide | $C_{17}H_{26}ClNO_3$ | — | C<br>H<br>N<br>Cl | 62.28<br>7.99<br>4.27<br>10.81 | 62.33<br>8.04<br>4.27<br>10.82 |
| 135 | N-(n-propoxymethyl)-2'-methoxy-3',6'-dimethyl-2-chloroacetanilide | $C_{15}H_{22}ClNO_3$ | 105 (0.03) | C<br>H<br>Cl | 60.10<br>7.40<br>11.83 | 60.14<br>7.40<br>11.82 |
| 136 | N-(isobutoxymethyl)-2'-methoxy-3',6'-dimethyl-2-chloroacetanilide | $C_{16}H_{24}ClNO_3$ | 107 (0.02) | C<br>H<br>Cl | 61.24<br>7.71<br>11.30 | 61.24<br>7.72<br>11.28 |
| 137 | N-(isopropoxymethyl)-2'-methoxy-3'6'-dimethyl-2-chloroacetanilide | $C_{15}H_{22}ClNO_2$ | 95 (0.03) | C<br>H<br>Cl | 60.10<br>7.40<br>11.83 | 59.99<br>7.40<br>11.86 |
| 138 | N-(allyloxymethyl)-2'- | $C_{16}H_{20}ClNO_3$ | 116 | C | 62.03 | 61.98 |

TABLE I-continued

| Example No. | Compound | Empirical Formula | B.P. °C. (mm Hg) | Element | Analysis Calculated | Found |
|---|---|---|---|---|---|---|
| | allyloxy-6'-methyl-2-chloroacetanilide | | (0.03) | H | 6.51 | 6.53 |
| | | | | Cl | 11.44 | 11.44 |
| 139 | N-(isobutoxymethyl)-2'-allyloxy-6'-methyl-2-chloroacetanilide | $C_{17}H_{24}ClNO_3$ | 120 (0.02) | C | 62.67 | 62.72 |
| | | | | H | 7.42 | 7.47 |
| | | | | Cl | 10.89 | 10.85 |
| 140 | N-(n-propoxymethyl)-2'-allyloxy-6'-methyl-2-chloroacetanilide | $C_{16}H_{22}ClNO_3$ | 121 (0.03) | C | 61.63 | 61.68 |
| | | | | H | 7.11 | 7.15 |
| | | | | Cl | 11.37 | 11.37 |
| 141 | N-(1-methylpropyloxymethyl)-2'-allyloxy-6'-methyl-2-chloroacetanilide | $C_{17}H_{24}ClNO_3$ | 115 (0.03) | C | 62.67 | 62.68 |
| | | | | H | 7.42 | 7.43 |
| | | | | Cl | 10.88 | 10.87 |
| 142 | N-(1-methylpropyloxymethyl)-2'-n-butyl-2-chloroacetanilide | $C_{17}H_{26}ClNO_3$ | 115 (0.02) | C | 62.28 | 62.18 |
| | | | | H | 7.99 | 8.03 |
| | | | | Cl | 10.81 | 10.80 |
| 143 | N-(ethoxymethyl)-2',6'-dimethyl-2-phenyl-2-chloroacetanilide | $C_{19}H_{22}ClNO_2$ | — | C | 68.77 | 68.55 |
| | | | | H | 6.68 | 6.72 |
| | | | | N | 4.22 | 4.21 |
| | | | | Cl | 10.68 | 10.64 |
| 144 | N-(n-propoxymethyl)-2'-ethoxy-2-phenyl-2-chloroacetanilide | $C_{20}H_{24}NO_3$ | — | C | 66.38 | 66.38 |
| | | | | H | 6.69 | 6.72 |
| | | | | N | 3.87 | 3.85 |
| | | | | Cl | 9.80 | 9.77 |
| 145 | N-(methoxymethyl)-2'-methoxy-6',2-dimethyl-2-chloroacetanilide | $C_{13}H_{18}ClNO_3$ | 47–62 (m.p.) | C | 57.46 | 57.40 |
| | | | | H | 6.68 | 6.68 |
| | | | | N | 5.15 | 5.16 |
| | | | | Cl | 13.05 | 13.02 |
| 146 | N-(isopropoxymethyl)-2'-methoxy-6',2-dimethyl-2-chloroacetanilide | $C_{15}H_{22}ClNO_3$ | 73–75 (m.p.) | C | 60.10 | 60.04 |
| | | | | H | 7.40 | 7.46 |
| | | | | N | 4.67 | 4.64 |
| | | | | Cl | 11.83 | 11.85 |
| 147 | N-(ethoxycarbonylmethyl)-2'-methoxy-6'-methyl-2-chloroacetanilide | $C_{14}H_{18}ClNO_4$ | 120 (0.02) | C | 56.10 | 55.99 |
| | | | | H | 6.05 | 6.09 |
| | | | | Cl | 11.83 | 11.81 |
| 148 | N-(ethoxycarbonylmethyl)-2'-n-butoxy-6'-methyl-2-bromoacetanilide | $C_{17}H_{24}BrNO_4$ | 132 (0.04) | C | 52.92 | 52.86 |
| | | | | H | 6.27 | 6.26 |
| | | | | Br | 20.67 | 20.69 |
| 149 | N-(ethoxymethyl)-N-(2,4-dimethyl-2-penten-3-yl)-2-chloroacetanilide | $C_{12}H_{22}ClNO_2$ | 90–111 (0.04) | C | 58.17 | 58.09 |
| | | | | H | 8.95 | 8.97 |
| | | | | N | 5.65 | 5.57 |
| 150 | N-(isopropoxymethyl)-N-(3-methyl-2-buten-2-yl)-2-chloroacetamide | $C_{11}H_{20}ClNO_2$ | 110–125 (0.07) | C | 56.53 | 56.29 |
| | | | | H | 8.62 | 8.83 |
| | | | | N | 5.99 | 5.62 |
| 151 | N-(n-butoxymethyl)-N-(3-methyl-2-buten-2-yl)-2-chloroacetamide | $C_{12}H_{22}ClNO_2$ | — | C | 58.17 | 57.99 |
| | | | | H | 8.95 | 8.96 |
| | | | | N | 5.65 | 5.33 |
| 152 | N-methyl-2'-isopentoxy-6'-methyl-2-chloroacetanilide | $C_{15}H_{22}ClNO_2$ | 120 (0.05) | C | 63.48 | 63.38 |
| | | | | H | 7.81 | 7.80 |
| | | | | Cl | 12.49 | 12.44 |
| 153 | N-methyl-2'-n-propoxy-6'-methyl-2-chloroacetanilide | $C_{13}H_{18}ClNO_2$ | 130 (0.15) | C | 61.05 | 60.88 |
| | | | | H | 7.09 | 7.12 |
| | | | | Cl | 13.86 | 13.70 |
| 154 | N-(2-chloroallyl)-2'-n-propoxy-6'-methyl-2-chloroacetanilide | $C_{15}H_{19}Cl_2NO_2$ | 128 (0.03) | C | 56.97 | 57.13 |
| | | | | H | 6.06 | 6.14 |
| | | | | Cl | 22.42 | 22.26 |
| 155 | N-(isopropoxymethyl)-2'-(trifluoromethyl)-2-chloroacetanilide | $C_{13}H_{15}F_3ClNO_2$ | 100–101 (0.05) | C | 50.41 | 50.52 |
| | | | | H | 4.88 | 4.89 |
| | | | | N | 4.52 | 4.56 |
| 156 | N-(isobutoxymethyl)-2'-(trifluoromethyl)-2-chloroacetanilide | $C_{14}H_{17}F_3ClNO_2$ | 120–125 (0.05) | C | 51.94 | 52.35 |
| | | | | H | 5.29 | 5.38 |
| | | | | N | 4.33 | 4.26 |
| 157 | N-(ethoxymethyl)-2'-(trifluoromethyl)-6'-methyl-2-chloroacetanilide | $C_{13}H_{15}F_3ClNO_2$ | 100–110 (0.1) | C | 50.41 | 50.02 |
| | | | | H | 4.88 | 4.81 |
| | | | | N | 4.52 | 4.38 |
| 158 | N-(ethoxymethyl)-2'-(2-ethoxyethoxy)-6'-isopropyl-2-chloroacetanilide | $C_{18}H_{28}ClNO_4$ | 128 (0.03) | C | 60.41 | 60.36 |
| | | | | H | 7.89 | 7.91 |
| | | | | Cl | 9.91 | 9.92 |
| 159 | N-(n-propoxymethyl)-2'-methoxyethoxy-6'-methyl-2-chloroacetanilide | $C_{16}H_{24}ClNO_4$ | — | C | 58.27 | 58.18 |
| | | | | H | 7.33 | 7.34 |
| | | | | N | 4.25 | 4.25 |
| | | | | Cl | 10.75 | 10.67 |
| 160 | N-(isopropoxymethyl)-2'-methoxyethoxy-6'-methyl-2-chloroacetanilide | $C_{16}H_{24}ClNO_4$ | — | C | 58.27 | 58.09 |
| | | | | H | 7.33 | 7.28 |
| | | | | N | 4.25 | 4.26 |
| | | | | Cl | 10.75 | 10.79 |
| 161 | N-(methoxymethyl)-2'-methoxyethoxy-6'-methyl-2-chloroacetanilide | $C_{10}H_{20}ClNO_4$ | — | C | 55.73 | 55.76 |
| | | | | H | 6.68 | 6.68 |
| | | | | Cl | 11.75 | 11.81 |
| 162 | N-methyl-2'-n-butoxy-6'-ethyl-2-chloroacetanilide | $C_{15}H_{22}ClNO_2$ | 115 (0.5) | C | 63.48 | 63.52 |
| | | | | H | 7.81 | 7.83 |
| | | | | Cl | 12.49 | 12.52 |

TABLE I-continued

| Example No. | Compound | Empirical Formula | B.P. °C. (mm Hg) | Element | Analysis Calculated | Found |
|---|---|---|---|---|---|---|
| 163 | N-(ethoxymethyl)-2'-methyl-6'-ethyl-2-chloroacetanilide | $C_{14}H_{20}ClNO_2$ | 125-130 (0.3) | C<br>H<br>Cl | 62.30<br>7.50<br>13.10 | 62.40<br>7.60<br>13.30 |
| 164 | N-(n-butoxymethyl)-2',6'-diethyl-2-chloroacetanilide | $C_{17}H_{26}ClNO_2$ | 156 (0.5) | C<br>H<br>Cl | 65.50<br>8.40<br>11.40 | 65.60<br>8.60<br>11.40 |
| 165 | N-(ethoxymethyl)-N-(2(6)-ethyl-6(2)-methyl-1-cyclohexen-1-yl)-2-chloroacetamide. (isomeric mixture 70% 6-ethyl isomer, 30% 2-ethyl isomer) | $C_{14}H_{24}ClNO_2$ | 136 (0.05) | C<br>H<br>N | 61.42<br>8.84<br>5.12 | 61.38<br>8.84<br>5.07 |
| 166 | N-(ethoxymethyl)-N-benzothiazoyl-2-yl)-2-chloroacetamide | $C_{12}H_{13}ClN_2O_2S$ | 139-141 (m.p.) | C<br>H<br>N | 50.61<br>4.60<br>9.84 | 50.80<br>4.60<br>9.89 |
| 167 | N-(methoxymethyl)-N-[3-chloro-1-(ethoxymethyl)-1,2-dihydro-2-oxo-4-quinolinyl]-2-chloroacetamide | $C_{12}H_{13}ClN_2O_2S$ | 100-102 (m.p.) | C<br>H<br>N | 51.49<br>4.86<br>7.51 | 50.69<br>4.79<br>7.42 |
| 168 | N-(acetamidomethyl)-N-(2,6-dimethyl-1-cyclohexen-1-yl)-2-chloroacetamide | $C_{13}H_{21}ClN_2O_2$ | 110-112 (m.p.) | C<br>H<br>N | 57.24<br>7.76<br>10.27 | 57.26<br>7.76<br>10.28 |
| 169 | N-(N',N'-dimethylcarbamoylmethyl)-N-2,6-dimethyl-1-cyclohexen-1-yl)-2-chloroacetamide. | $C_{14}H_{23}ClN_2O_2$ | | | | |
| 170 | N-(N'-methyl-N'-ethoxycarbamoylmethyl)-2',6'-dimethyl-2-chloroacetanilide | $C_{15}H_{21}ClN_2O_3$ | 80-82 (m.p.) | | | |
| 171 | N-(methoxymethyl)-2'-methyl-6'-ethoxy-2-chloroacetanilide | $C_{13}H_{18}ClNO_3$ | 181-184 (0.8) | C<br>H<br>N<br>Cl | 57.46<br>6.68<br>5.15<br>13.04 | 57.38<br>6.69<br>5.14<br>13.05 |
| 172 | N-(ethoxymethyl)-N-(2-methoxy-3-pyridyl)-2-chloroacetamide | $C_{10}H_{15}ClN_2O_3$ | 80 (0.05) | C<br>H<br>Cl | 51.07<br>5.84<br>13.70 | 51.55<br>5.78<br>12.47 |
| 173 | N-(ethoxymethyl)-N-(4,6-dimethoxy-2-trifluoromethyl-3-pyridyl)-2-chloroacetamide | $C_{13}H_{16}ClF_3N_2O_3$ | 72-73 (m.p.) | C<br>H<br>N | 43.77<br>4.52<br>7.85 | 43.74<br>4.45<br>7.88 |
| 174 | N-methyl-N-(4,6-dimethoxy-2-trifluoromethyl-3-pyridyl) 2-chloroacetamide | $C_{11}H_{12}ClF_3N_2O_3$ | 72-73 (m.p.) | C<br>H<br>N | 42.26<br>3.87<br>8.96 | 42.44<br>3.84<br>8.98 |
| 175 | N-methyl-2'-isopropoxy-6'-methyl-2-chloroacetanilide | $C_{13}H_{18}ClNO_2$ | 127 (0.03) | C<br>H<br>Cl | 61.05<br>7.09<br>13.86 | 61.05<br>7.09<br>13.83 |
| 176 | N-(methoxymethyl)-2'-(trimethylsilyl)-6'-methyl-2-chloroacetanilide | $C_{14}H_{22}ClNO_2Si$ | | | | |

The process according to this invention is of wide applicability as indicated in the preparation of the compounds in the above examples. Still further, the process of this invention may be suitably used to prepare a variety of other tertiary 2-haloacetamides from the anion (negative charge on nitrogen atom) of primary or secamides thereof. For example, the present process may be used to prepare N-(alkoxyalkyl)-N-(1-alken-1-yl)-2-haloacetamides such as N-(methoxyethyl)-N-(1-isopropyl-2-methyl-1-propen-1-yl)-2-chloroacetamide; N-(methoxyethyl)-N-(1-isopropyl-1-propen-1-yl)-2-chloroacetamide; N-(methoxyethyl)-N-(1-methylpropen-1-yl)-2-chloroacetamide; N-(methoxyethyl)-N-(1-ethylbuten-1-yl)-2-chloroacetamide; N-(methoxyethyl)-N-(1-isopropylvinyl)-2-chloroacetamide and N-(methoxyethyl)-N-(1-n-propylpropen-1-yl)-2-chloroacetamide. These and analogous compounds having from $C_2-C_6$-alkoxyalkyl radicals are disclosed in the above-mentioned South African Patent No. 753918. However, as discussed above, the process of said '918 patent is not amenable to the production of analogous N-alkoxymethyl compounds because of the non-existence of the necessary N-(alkoxymethyl)-substituted primary amine required to perform the process disclosed in that patent. The process of the present invention permits the production of N-(alkoxmethyl)-N-(1-alken-1-yl)-2-haloacetamides for the first time, as well as the N-($C_2-C_6$-alkoxyethyl)-haloacetamides of said '918 patent. Exemplary of such N-(alkoxymethyl) acetamide compounds (in addition to those shown in Examples 23 24, and 150, 151 of Table I) are the methoxymethyl, ethoxymethyl, n- and isopropoxymethyl and n-, iso- and t-butoxymethyl and pentoxymethyl homologs of the above alkoxyethyl compounds and other homologs having still other alkenyl radicals attached to the N atom; said alkenyl radicals can be substituted with alkyl, cycloalkyl, alkenyl, alkynyl, aryl, aralkyl or heterocyclic radicals. Similarly, as indicated above, whereas the process of U.S. Pat. No. 3,574,746 is capable of producing N-alkoxyethyl-N-(1-cycloalken-1-yl)-2-chloroacetamides, that process cannot be used to produce the homologous N-(alkoxymethyl) compounds because of the non-existence of the necessary N-(alkoxymethyl)-N-cycloalkylidene amine starting material. The process of the present invention is amendable to the preparation of N-(alkoxymethyl)-N-(1-cycloalken-1-yl)-2-haloacetamides for the first time, as well as the N-($C_2$-$C_8$-alkoxyalkyl)-N-(1-cycloalken-1-yl)-2-haloacetamides of said '746 patent.

In like manner the process of this invention may also be used to prepare N-heterocyclylmethyl-2-haloacetanilides such as N-(2,4-dioxothiazolidin-3-ylmethyl)-2-haloacetanilides, exemplified specifically by 2-chloro-N-(2,4-dioxothiazolidin-3-ylmethyl)-N-(2-methylphenyl) acetanilide and 2-chloro-N-(2,4-dioxothiazolidin-3-ylmethyl)-N-(2-methoxyphenyl) acetanilide. These and similar compounds are described in U.S. Pat. 4,055,410 which discloses a different process for their preparation, viz, haloacetylation of the corresponding sec-anilide in an aprotic solvent in the presence of an acid acceptor.

Within the carbon atom chain length limitations defined above for the various R members, i.e., R-$R_7$, inclusive, in Formulae I-IV, representative groups include as alkyls, methyl, ethyl, the various isomeric forms of propyls, butyls, pentyls, hexyls, heptyls, octyls, nonyls, decyls, undecyls, dodecyls, tridecyls, pentadecyls, octadecyls, etc., as alkenyls, e.g., vinyl, allyl, crotyl, methallyl, butenyls, pentyls, hexenyls, heptenyls, octenyls, nonenyls, decenyls, etc., as alkynyls, e.g., ethynyl, propynyls, butynyls, pentynyls, hexynyls, etc; the alkoxy, polyalkoxy, alkoxyalkyl and polyalkoxyalkyl analogs of the foregoing alkyl groups; cycloalkyls and cycloalkylalkyls having up to 7 cyclic carbons, e.g., cyclopropyl, cyclobutyl, cyclopentyl, cyclohexyl, cycloheptyl, cyclopropylmethyl, cyclobutylmethyl, cyclopentylmethyl, etc; cycloalkenyls and cycloalkadienyls having up to 7 cyclic carbons, e.g., cyclopentenes, cyclohexenes and cycloheptenes having mono- and di-unsaturation; $C_{6-10}$ aryl and aralkyl and alkaryl groups, e.g., phenyl, tolyls, xylyls, benzyl, naphthyl, etc., and said R members substituted with radicals which are non-reactive under reaction conditions, e.g., hydrogen, other R members, cyano, nitro, amino, trifluoromethyl, alkylthio, etc. Preferred aliphatic members are those having up to 12 carbon atoms.

The X member in Formulae I and II above comprises the halogen members chlorine, bromine and iodine, whereas the $X^1$ member comprises chlorine, bromine, iodine or a halogen equivalent derived from alkylating agents exemplified hereinabove.

The process of this invention is particularly amendable to the production of the subgenera of 2-haloacetamides described above as of particular interest.

Although many of the compounds defined by Formula I above are known compounds, certain of the 2-haloacetamides described herein are novel compounds and separately claimed by other inventors employed by the assignee herein.

It will be appreciated by those skilled in the art that the process of this invention may be modified in a manner within the skill of this art as to nature and concentration of reactants, reaction and separation conditions of temperature, pressure, residence times, etc., to produce other species of compounds not specifically named herein, but within the generic scope of this invention and its obvious equivalents.

I claim:

1. Process for the preparation of 2-haloacetamides having the formula

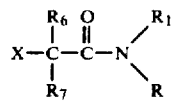

which comprises converting a secondary 2-haloacetamide of the formula

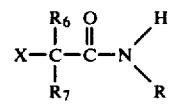

to an anion thereof under basic conditions by means of electrolysis or reaction with metal hydrides, fluorides, oxides, hydroxides, carbonates, phosphates, or alkoxides and reacting said anion with a compound of the formula $$R_1X^1 \qquad (III)$$

or a (1,4-)Michael addition reagent wherein in the above formulae:

X is chlorine, bromine or iodine;

$X^1$ is chlorine, bromine, iodine or a halogen equivalent;

R is hydrogen, $C_{1-18}$ alkyl, $C_{2-18}$ alkenyl, alkynyl or alkoxyalkyl, polyalkoxyalkyl, $C_{3-7}$ cycloalkyl or cycloalkylalkyl, $C_{5-7}$ cycloalkenyl or cycloalkadienyl which may be substituted with $C_{1-6}$ alkyl groups; saturated or unsaturated heterocyclic radicals having up to 6 ring atoms containing O, $S(O)_a$ and/or $N(R_5)_b$ groups; or a radical of the formula

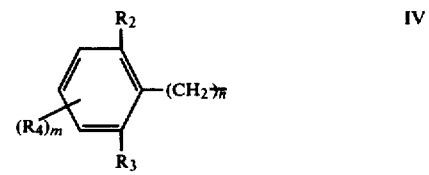

wherein
a is 0–2 inclusive;
b and n are 0 or 1;
m is 0–3 inclusive when $R_2$ and $R_3$ are other than hydrogen and 0–5 otherwise.

$R_2$, $R_3$, $R_4$ and $R_5$ are independently hydrogen, $C_{1-6}$ alkyl, alkoxy, polyalkoxy or alkoxyalkyl, $C_{2-6}$ alkenyl, alkenyloxy, alkynyl or alkynyloxy, $C_{6-10}$ aryl, aryloxy, aralkyl or aralkyloxy, $NO_2$, halogen, $CF_3$, $(CH_3)_3Si$-, saturated or unsaturated heterocyclic radical having up to 6 ring atoms containing O, $S(O)_a$ and/or $N(R_5)_b$ groups or $R_2$, $R_3$ or $R_4$ when combined with the phenyl radical to which attached may form a $C_{6-10}$ aryl radical; or, when not a hydrogen atom, the R group may be substituted with an $R_2$-$R_5$ group;

$R_1$ is $C_{1-18}$ alkyl, $C_{3-18}$ alkenyl or alkynyl, $C_{2-18}$ alkoxyalkyl, $C_{3-7}$ cycloalkyl or cycloalkylalkyl, $C_{6-10}$ aralkyl, alkylthiomethyl, cyanomethyl, loweracyloxymethyl, loweralkylthiocarbomethyl, substituted or unsubstituted carbamoylmethyl, benzothiazolinonylmethyl, phthalimidomethyl, mono- or di-loweracylamidomethyl or $C_{1-10}$ hydrocarbylsulfonylamidomethyl groups or said $R_1$ member substituted with an R$_2$-R$_5$ member which is inert under reaction conditions, provided that when R$_1$ is an alkenyl radical it cannot have an olefinic bond on the carbon atom attached to the nitrogen atom and R$_6$ and R$_7$ are independently hydrogen or alkyl, cycloalkyl, alkenyl, cycloalkenyl, or aromatic hydrocarbon each having up to 12 carbon atoms.

2. Process according to claim 1 wherein R$_1$ is an alkoxyalkyl radical having up to 12 carbon atoms.

3. Process according to claim 2 wherein R$_1$ is an alkoxymethyl radical and X and X$^1$ are independently chlorine or bromine.

4. Process according to claim 3 wherein R$_1$ is an alkoxymethyl radical and R is a radical having the formula

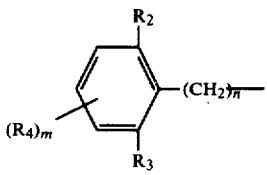

wherein m, n, R$_2$, R$_3$ and R$_4$ have the above meanings.

5. Process according to claim 4 wherein m and n are zero and R$_2$ and R$_3$ are independently hydrogen or C$_{1-6}$ alkyl radicals.

6. Process according to claim 5 wherein said 2-haloacetamide is N-(methoxymethyl)-2',6'-diethyl-2-chloroacetanilide.

7. Process according to claim 5 wherein said 2-haloacetamide is N-(n-butoxymethyl)-2',6'-diethyl-2-chloroacetanilide.

8. Process according to claim 5 wherein said 2-haloacetamide is N-(ethoxymethyl)-2'-methyl-6'-ethyl-2-chloroacetanilide.

9. Process according to claim 4 wherein R$_2$ is alkoxy, polyalkoxy or alkenyloxy having up to 6 carbon atoms, nitro or trifluoromethyl and R$_3$ and R$_4$ are independently hydrogen, alkyl, or an R$_2$ member.

10. Process according to claim 9 wherein said 2-haloacetamide is N-(isopropoxymethyl)-2'-methoxy-6'-methyl-2-chloroacetanilide.

11. Process according to claim 9 wherein said 2-haloacetamide is N-(ethoxymethyl)-2'-isopropoxy-6'-methyl 2-chloroacetanilide.

12. Process according to claim 9 wherein said 2-haloacetamide is N-(ethoxymethyl)-2'-n-propoxy-6'-methyl-2-chloroacetanilide.

13. Process according to claim 9 wherein said 2-haloacetamide is N-(n-propoxymethyl)-2'-methoxy-6'-methyl-2-chloroacetanilide.

14. Process according to claim 9 wherein said 2-haloacetamide is N-(isopropoxymethyl)-2'-methoxy-3',6'-dimethyl-2-chloroacetanilide.

15. Process according to claim 9 wherein said 2-haloacetamide is N-(allyloxymethyl)-2'-allyloxy-6'-methyl-2-chloroacetanilide.

16. Process according to claim 9 wherein said 2-haloacetamide is N-(1-methylpropoxymethyl)-2'-allyloxy-6'-methyl-2-chloroacetanilide.

17. Process according to claim 9 wherein said 2-haloacetamide is N-(n-propoxymethyl)-2'-isobutoxy-6'-methyl-2-chloroacetanilide.

18. Process according to claim 9 wherein said 2-haloacetamide is N-(isopropoxymethyl)-2'-trifluoromethyl-2-chloroacetanilide.

19. Process according to claim 9 wherein said 2-haloacetamide is N-(ethoxymethyl)-2'-trifluoromethyl-6'-methyl-2-chloroacetanilide.

20. Process according to claim 9 wherein said 2-haloacetamide is N-(n-propoxymethyl)-2'-(2-methoxyethoxy)-6'-methyl-2-chloroacetanilide.

21. Process according to claim 9 wherein said 2-haloacetamide is N-(isopropoxymethyl)-2'-(2-methoxyethoxy)-6'-methyl-2-chloroacetanilide.

22. Process according to claim 3 wherein R is a cycloalkenyl or cycloalkadienyl radical having up to 7 carbon atoms or such radicals substituted with one or more C$_{1-6}$ alkyl radicals.

23. Process according to claim 22 wherein R is a 1-cyclohexen-1-yl radical or such radical substituted with one or more C$_{1-6}$ alkyl radicals.

24. Process according to claim 23 wherein R is a 2,6-dimethyl-1-cyclohexen-1-yl radical.

25. Process according to claim 24 wherein said 2-haloacetamide is N-(isobutoxymethyl)-N-(2,6-dimethyl-1-cyclohexen-1-yl)-2-chloroacetamide.

26. Process according to claim 23 wherein said 2-haloacetamide is N-(n-butoxymethyl)-N-(2,6-diethyl-1-cyclohexen-1-yl)-2-chloroacetamide.

27. Process according to claim 23 wherein said 2-haloacetamide is an isomeric mixture of N-(ethoxymethyl)-N-(2-methyl-6-ethyl-1-cyclohexen-1-yl)-2-chloroacetamide and N-(ethoxymethyl)-N-(6-methyl-2-ethyl-1-cyclohexen-1-yl)-2-chloroacetamide.

28. Process according to claim 3 wherein R is an alkenyl radical having up to 18% carbon atoms.

29. Process according to claim 28 wherein said alkenyl radical has an olefinic bond on the carbon atom attached to the nitrogen atom.

30. Process according to claim 29 wherein said 2-haloacetamide is N-(ethoxymethyl)-N-(2,4-dimethyl-2-penten-3-yl)-2-chloroacetamide.

31. Process according to claim 29 wherein said 2-haloacetamide is N-(isopropoxymethyl)-N-(3-methyl-2-buten-2-yl)-2-chloroacetamide.

32. Process according to claim 29 wherein said 2-haloacetamide is N-(n-butoxymethyl)-N-(3-methyl-2-buten-2-yl)-2-chloroacetamide.

33. Process according to claim 2 wherein said alkoxyalkyl radical is an alkoxyethyl radical which may be substituted with one or more C$_{1-4}$ alkyl groups on said ethyl moiety and X and X$^1$ are independently chlorine or bromine.

34. Process according to claim 33 wherein R is a C$_{2-12}$ alkenyl radical which may be substituted with one or more C$_{1-6}$ alkyl, C$_{3-6}$ cycloalkyl or cycloalkylmethyl groups.

35. Process according to claim 24 wherein said alkenyl or substituted-alkenyl radical has an olefinic bond on the carbon atom attached to the nitrogen atom.

36. Process according to claim 35 wherein said 2-haloacetamide is N-(3-methyl-2-buten-2-yl)-N-(n-propoxyethyl)-2-chloroacetamide.

37. Process according to claim 35 wherein said 2-haloacetamide is N-(2,4-dimethyl-2-penten-3-yl)-N-(2-methoxyethyl)-2-chloroacetamide.

38. Process according to claim 33 wherein R is a radical having the formula

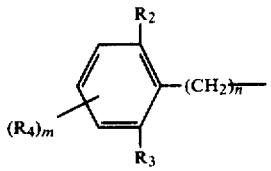

wherein m, n, $R_2$, $R_3$ and $R_4$ have the above meanings.

39. Process according to claim 38 wherein m and n are zero and $R_2$, $R_3$ and $R_4$ are independently hydrogen or $C_{1-6}$ alkyl radicals.

40. Process according to claim 38 wherein m and n are zero, $R_2$ is alkoxy, polyalkoxy or alkenyloxy having up to 6 carbon atoms, nitro or trifluoromethyl and $R_3$ and $R_4$ are independently hydrogen, alkyl or an $R_2$ member.

41. Process according to claim 33 wherein R is a cycloalkenyl, or cycloalkadienyl radical having up to 7 carbon atoms which may be substituted with $C_{1-6}$ alkyl radicals.

42. Process according to claim 1 wherein $R_1$ is a $C_{1-18}$ alkyl radical.

43. Process according to claim 42 wherein R is a radical having the formula

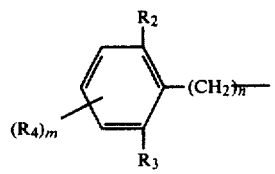

wherein m, n, $R_2$, $R_3$ and $R_4$ have the above meanings.

44. Process according to claim 43 wherein m and n are zero and $R_2$, $R_3$ and $R_4$ are independently hydrogen or $C_{1-6}$ alkyl radicals.

45. Process according to claim 43 wherein m and n are zero, $R_2$ is alkoxy, polyalkoxy or alkenyloxy having up to 6 carbon atoms, nitro or trifluoromethyl and $R_3$ and $R_4$ are independently hydrogen, alkyl or an $R_2$ member.

46. Process according to claim 45 wherein said 2-haloacetamide is N-methyl-2'-butoxy-6'-methyl-2-chloroacetanilide.

47. Process according to claim 45 wherein said 2-haloacetamide is N-methyl-2'-isobutoxy-6'-methyl-2-chloroacetanilide.

48. Process according to claim 45 wherein said 2-haloacetamide is N-methyl-2'-n-propoxy-6'-methyl-2-chloroacetanilide.

49. Process according to claim 45 wherein said 2-haloacetamide is N-methyl-2'-n-butoxy-6'-ethyl-2-chloroacetanilide.

50. Process according to claim 1 wherein $R_1$ is an alkenyl or haloalkenyl radical having up to 12 carbon atoms.

51. Process according to claim 50 wherein R is a radical of Formula IV.

52. Process according to claim 1 wherein $R_1$ is an alkynyl radical having up to 12 carbon atoms.

53. Process according to claim 52 wherein R is a radical of Formula IV.

54. Process according to claim 52 wherein R is an alkenyl radical having up to 12 carbon atoms.

55. Process according to claim 1 wherein $R_1$ is a heterocyclyl or heterocyclylmethyl radical having up to 6 ring atoms containing O, S and/or N atoms.

56. Process according to claim 55 wherein R is a radical of Formula IV.

57. Process according to claim 55 wherein R is a cycloalkenyl or cycloalkadienyl radical having up to 7 carbon atoms.

58. Process according to claim 57 wherein said 2-haloacetamide is N-(2,6-dimethyl-1-cyclohexen-1-yl)-N-[3-(2-benzothiazolinone) methyl]-2-chloroacetamide.

59. Process according to claim 1 wherein the initial product mixture is recycled after an acid wash to regenerate starting sec-amide from by-product imidate, and then reacted with additional compound of Formula III.

60. Process according to claim 1 wherein said amide anion is generated by an alkali metal hydride.

61. Process according to claim 60 wherein said alkali metal hydride is potassium hydride.

62. Process according to claim 1 wherein said amide anion is generated by an alkali metal hydroxide or alkaline earth hydroxide.

63. Process according to claim 62 wherein said alkali metal hydroxide is aqueous sodium hydroxide.

64. Process according to claim 62 wherein said alkali metal hydroxide is solid potassium hydroxide.

65. Process according to claim 1 wherein said alkali metal carbonate is solid potassium carbonate.

66. Process according to claim 1 wherein said amide anion is generated by an alkali metal fluoride.

67. Process according to claim 66 wherein said alkali metal fluoride is potassium fluoride.

68. Process according to any of Claims 60–67 wherein said reaction is conducted in the presence of a phase transfer catalyst.

69. Process according to claim 68 wherein said catalyst is a quaternary ammonium halide salt.

70. Process according to claim 69 wherein said salt is a benzyl trialkyl ammonium halide salt.

71. Process according to claim 68 wherein said catalyst is a polyether.

72. Process according to claim 71 wherein said polyether is a cyclic polyether.

73. Process according to claim 1 wherein said anion is generated by electrolysis.

74. Process according to claim 9 wherein said 2-haloacetamide is N-(-1-methylpropoxymethyl)-2'1 -n-butoxy-2-chloroacetanilide.

75. Process according to claim 45 wherein said 2-haloacetamide is N-methyl-2'-isopropoxy-6'-methyl-2-chloroacetanilide.

* * * * *